United States Patent [19]
Alizon et al.

[11] Patent Number: 6,054,565
[45] Date of Patent: Apr. 25, 2000

[54] NUCLEIC ACIDS OF HIV-2, DIAGNOSTIC TEST KIT AND METHOD USING NUCLEIC ACID PROBES OF HIV-2

[75] Inventors: Marc Alizon, Paris; Luc Montagnier, Le Plessis Robinson; Denise Geutard, Paris, all of France; Francois Clavel, Rockville, Md.; Pierre Sonigo; Mireille Guyader, both of Paris, France

[73] Assignee: Institut Pasteur, France

[21] Appl. No.: 08/234,875

[22] Filed: Apr. 28, 1994

Related U.S. Application Data

[62] Division of application No. 07/810,908, Dec. 20, 1991, which is a division of application No. 07/752,368, Sep. 3, 1991, abandoned, which is a division of application No. 07/013,477, Feb. 11, 1987, Pat. No. 5,079,342, which is a continuation-in-part of application No. 07/003,764, Jan. 16, 1987, Pat. No. 5,051,496, which is a continuation-in-part of application No. 06/933,184, Nov. 21, 1986, abandoned, which is a continuation-in-part of application No. 06/916,080, Oct. 6, 1986, abandoned, which is a continuation-in-part of application No. 06/835,228, Mar. 3, 1986, Pat. No. 4,839,288.

[51] Int. Cl.$^7$ .......................... C07H 21/02; C07H 21/04; C12Q 1/68

[52] U.S. Cl. ............................. 536/23.1; 435/5; 436/501; 536/24.1; 536/24.3; 536/24.31; 536/24.32; 536/24.33; 935/77; 935/78

[58] Field of Search ................................ 435/5, 6, 320.1, 435/810; 436/501; 536/22.1, 23.1, 24.1, 24.31–24.33; 935/77, 78

[56] References Cited

U.S. PATENT DOCUMENTS

| | | | |
|---|---|---|---|
| 4,629,783 | 12/1986 | Cosand | 530/324 |
| 4,839,288 | 6/1989 | Montagnier et al. | 435/235 |
| 5,051,496 | 9/1991 | Alizon et al. | 530/324 |
| 5,079,342 | 1/1992 | Alizon et al. | 530/324 |
| 5,223,423 | 6/1993 | Franchini et al. | 435/236 |
| 5,310,651 | 5/1994 | Alizon et al. | 435/6 |

FOREIGN PATENT DOCUMENTS

| | | |
|---|---|---|
| 0 316 695 B1 | 3/1993 | European Pat. Off. |
| WO 85/04897 | 11/1985 | WIPO |

OTHER PUBLICATIONS

Clavel et al. (1986) Nature, vol. 324, pp. 691–695.
Clavel et al., "Isolation of a New Human Retrovirus from West African Patients with AIDS," *Science*, 233, pp. 343–346 (1986).
Allan et al., "Major Glycoprotein Antigens That Induce Antibodies in AIDS Patients Are Encoded by HTLV–III," *Science*, 228, pp. 1091–1094 (1985).
Chang et al., "Detection of Antibodies to Human T–Cell Lymphotropic Virus–III (HTLV–III) with an Immunoassay Employing a Recombinant *Escherichia coli*–Derived Viral Antigenic Peptide," *Bio/Technology*, 3, pp. 905–909 (1985).
Kanki et al., "Isolation of T–lymphotropic Retrovirus Related to HTLV–III/LAV from Wild–Caught African Green Monkeys, "*Science*, 230, pp. 951–954.
Kanki et al., "Serologic Identification and Characterization of a Macaque T–lymphotropic Retroviurs Closely Related to HTLV–III, "*Science*, 228, pp. 1199–1201 (1985).
Clavel et al., "LAV Type II: A Second Retrovirus Associated With AIDS In West Africa," *C.R. Acad. Sc. Paris*, Serie III, 302, pp. 485–488 (1986).
Klatzmann et al., "T–lymphocyte T4 Molecule Behaves As The Receptor For Human Retrovirus LAV," *Nature*, 312, pp. 767–768 (1984).

(List continued on next page.)

*Primary Examiner*—Ardin H. Marschel
*Attorney, Agent, or Firm*—Finnegan, Henderson, Farabow, Garrett & Dunner, L.L.P.

[57] ABSTRACT

A method for diagnosing an HIV-2 (LAV-II) infection and a kit containing reagents for the same is disclosed. These reagents include cDNA probes which are capable of hybridizing to at least a portion of the genome of HIV-2. In the embodiment, the DNA probes are capable of hybridizing to the entire genome of HIV-2. These reagents also include polypeptides encoded by some of these DNA sequences.

2 Claims, 5 Drawing Sheets

OTHER PUBLICATIONS

Daniel et al., "Isolation of T–Cell Tropic HTLV–III–like Retrovirus from Macaques,"*Science*, 228, pp. 1201–1204 (1985).

Barin et al., "Serological Evidence For Virus Related To Simian T–lymphotropic Retrovirus III in Residents of West Africa," *The Lancet*, pp. 1387–1389 (Dec. 21/28, 1985).

Sandstrom et al., "Antiviral Therapy In AIDS Clinical Pharmacological Properties and Therapeutic Experience to Date,"*Drugs*, 34, pp. 372–390 (1987).

Mitsuya et al., "Protection of T Cells Against Infectivity and Cytopathic Effect of HTLV–III In Vitro," Retroviruses in Human Lymphoma/Leukemia, M. Miwa et al., eds., pp. 277–288 (Japan Science Press, Tokyo, 1985).

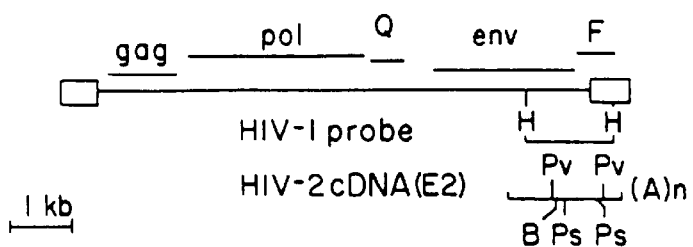
FIG. IA
FIG. IB

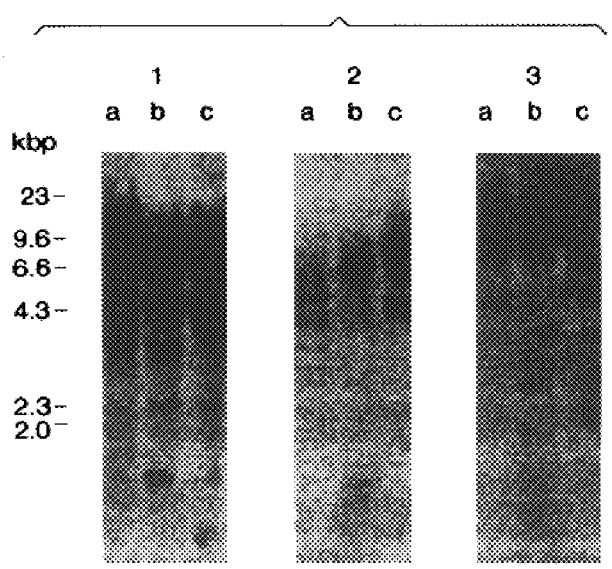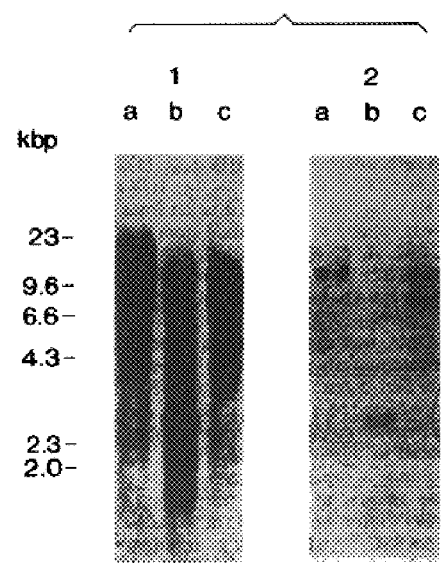

NUCLEIC ACIDS OF HIV-2, DIAGNOSTIC TEST KIT AND METHOD USING NUCLEIC ACID PROBES OF HIV-2

This application is a divisional application of Ser. No. 07/801,908, filed Dec. 20, 1991, still pending, which is a divisional application of Ser. No. 07/752,368, filed Sep. 3, 1991, now abandoned, which is a divisional application of Ser. No. 07/013,477, filed Feb. 11, 1987, now U.S. Pat. No. 5,079,342, which is a continuation-in-part application of Ser. No. 07/003,764, filed Jan. 16, 1987, now U.S. Pat. No. 5,051,496, which is a continuation-in-part application of Ser. No. 06/933,184, filed Nov. 21m 1986, now abandoned, which is continuation-in-part application of Ser. No. 06/916,080, filed Oct. 6, 1986, now abandoned, which is a continuation-in-part application of Ser. No. 06/835,228, filed Mar. 3, 1986, now U.S. Pat. No. 4,839,288.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a subsequently-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, now U.S. Pat. No. 4,839,288 and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolates, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, other with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnoising an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages my be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

In accordance with a further object of the present invention, a peptide is provided as described above, either alone or conjugated to a carrier molecule, the peptide being capable of eliciting the production of an antibody to the peptide, and said antibody is capable of forming an effective immunocomplex with the entire HIV-2 retrovirus or with its corresponding proteins.

To further achieve the objects of the invention, a vaccinating agent is provided which comprises at least one peptide selected from the polypeptide expression products of the viral DNA in admixture with suitable carriers, adjuvants stabilizers.

It is understood that both the foregoing general description and the following detailed description are exemplary and explanatory only and are not restrictive of the invention as claimed. The accompanying drawings, which are incorporated in and constitute a part of the specification, illustrative one embodiment of the invention and, together with the description, serve to explain the principles of the invention.

BRIEF DESCRIPTION OF THE DRAWINGS

FIGS. 1A and 1B generally depict the nucleotide sequence of a cloned complementary DNA (cDNA) to the genomic RNA of HIV-2. FIG. 1A depicts the genetic organization of HIV-1, position of the HIV-1 HindIII fragment used as a probe to screen the cDNA, library, and restriction map of the HIV-2 cDNA clone, E2. FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in *Proc. Natl. Acad. Sci. USA* 80: 726–730 (1983), specifically incorporated herein by reference. The U3-R junction in HIV-1 is indicated and the poly A addition signal and potential TATA promoter regions are boxed. In FIG. 1A, the symbols B, H, Ps and Pv refer to the restriction sites BamHI, HindIII, PstI and PvuII, respectively.

FIGS. 2A–2D generally depict the HIV-2 specificity of the E2 clone. FIG. 2A and B are line drawings representing Southern Blots of DNA extracted from CEM cells infected with the following isolates: HIV-$2_{ROD}$ (a,c), HIV-$2_{DUL}$ (b,d) and HIV-$1_{BRU}$ (e,f). DNA in lanes a,b,f was Pst I digested; in c,d,e DNA was undigested. FIG. 2C and D are line drawings representing dot blot hybridization of pelleted virions from CEM cells infected by the HIV-$1_{BRU}$(1), Simian Immunodeficiency Virus (SIV) isolate Mm 142–83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIG. 2A and C depict hybridization with the HIV-2 cDNA (E2) and FIG. 2B and D depict hybridization to an HIV-1 probe consisting of a 9 Kb SacI insert from HIV-1 BRU(clone lambda J 19).

FIGS. 3A and 3B generally depict a restriction map of the HIV-2 ROD genome and its homology to HIV-1. FIG. 3A specifically depicts the organization of three recombinant phage lambda clones, ROD 4, ROD 27, and ROD 35. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 3B specifically depicts dots 1–11 which correspond to the single-stranded DNA form of M13 subclones from the HIV-$1_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2× SSC, 0.1% SDS at 25° C. (Tm −42° C.), 1× SSC, 0.1% SDS at 60° C. (Tm −20° C.), and 0.1× SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-$1_{BRU}$ genome. HIV-1 and HIV-2 probes were labelled the same specific activity ($10^8$ cpm/ g.).

FIGS. 4A and 4B generally depict the restriction map polymorphism in different HIV-2 isolates and shows comparison of HIV-2 to SIV. FIG. 4A is a line drawing depicting DNA (20 μg per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/μg.

FIG. 4B is a line drawing depicting DNA from HUT 78 (a human T lymphoid cell line) cells infected with STLV3 MAC isolates Mm 142–83. The same amounts of DNA and enzymes were used as indicated in panel A. Hybridization was performed with the same probe as in A, but in non-stringent conditions. As described in Example 1 washing was for one hour in 2× SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.

FIG. 5 depicts the position of derived plasmids from λROD 27, λROD 35 and λROD 4.

DETAILED DESCRIPTION OF THE PREFERRED EMBODIMENTS

Reference will now be made in detail to the presently preferred embodiments of the invention, which, together with the following examples, serve to explain the principles of the invention.

The genetic structure of the HIV-2 virus has been analyzed by molecular cloning according to the method set forth herein and in the Examples. A restriction map of the genome of this virus is included in FIG. 5. In addition, the partial sequence of a cDNA complementary to the genomic RNA of the virus has been determined. This cDNA sequence information is included in FIG. 1.

Also contained herein is data distributing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described in S. Wain Hobson et al. in Cell 40: 9–17 (1985), specifically incorporated herein by reference. The portion of the HIV-2 LTR that was sequenced was related only distantly to the homologous domian in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

Figure 2A:
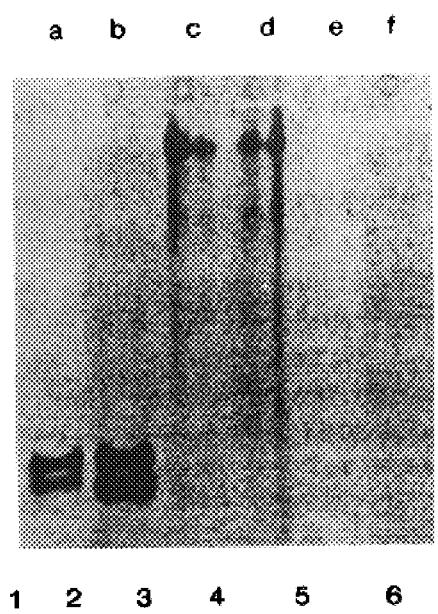
Figure 2B:
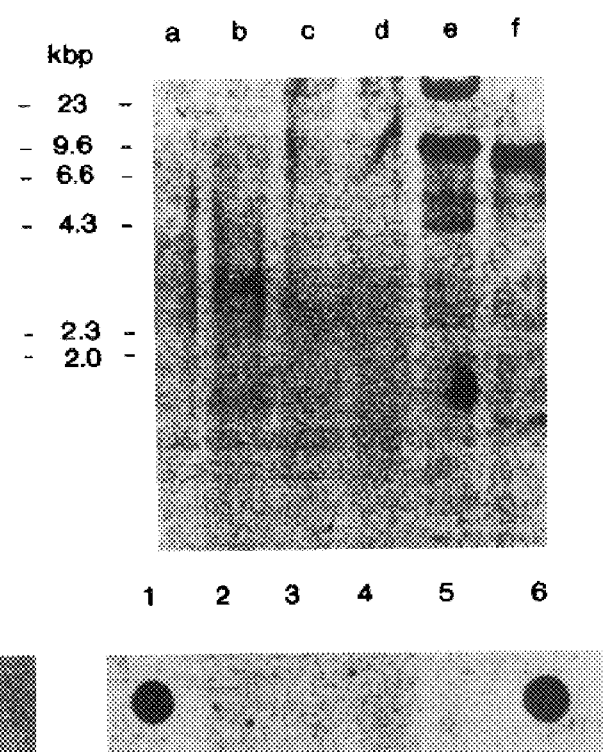
Figure 2C:

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2C and D. Secondly, positive signals were detected in Southern blots of DNA from cells infected with the ROD isolate as well as other isolates of HIV-2 as shown in FIG. 2A and FIG. 4A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-$2_{ROD}$.

About $2\times10^6$ recombinant plaques were screened in situ with labelled insert from the E2 cDNA clone. Ten recombinant phages were detected and plaque purified. Of these plaques, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
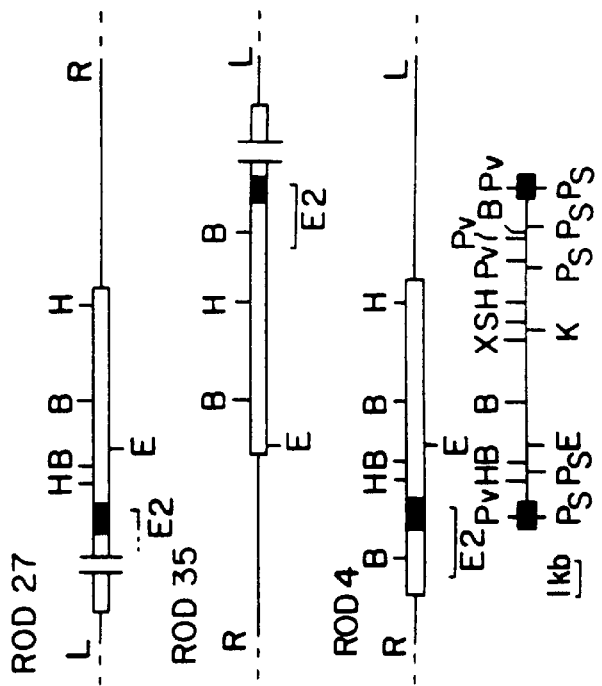
Figure 3B:
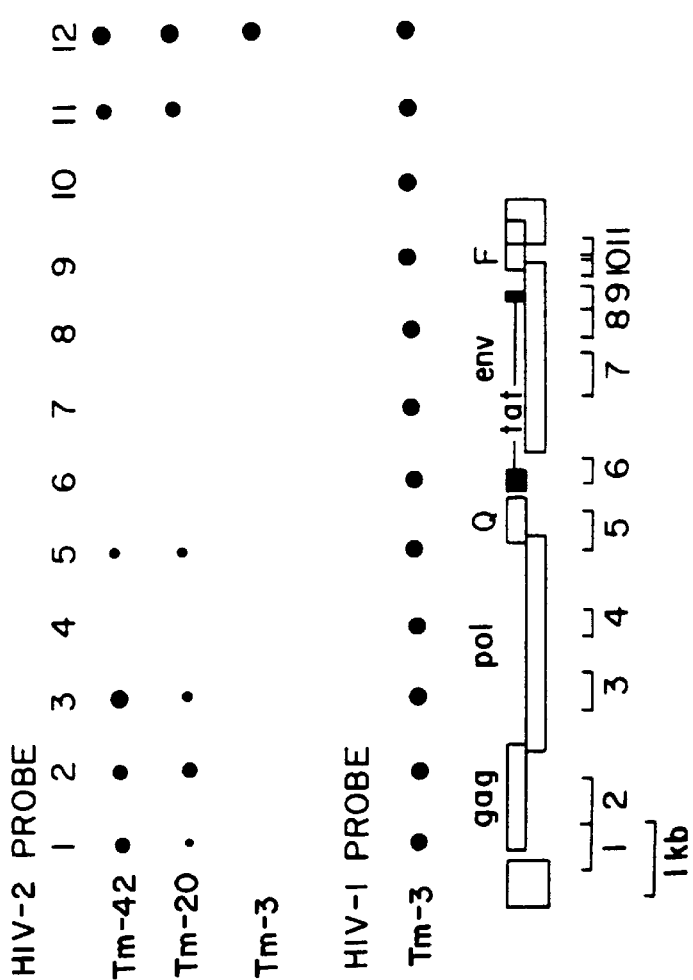

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3A.

Fragments of the lambda clones were subcloned into a plasmid vector p UC 18.

Plasmid pROD 27-5' is derived from λROD 27 and contains the 5' 2 Kb of the HIV-2 genome and cellular flanking sequences (5' LTR and 5' viral coding sequences to the EcoRI site)

Plasmid p ROD 4–8 is derived from λROD 4 and contains the about 5 Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 Kb of cellular flanking sequences.

Figure 5:
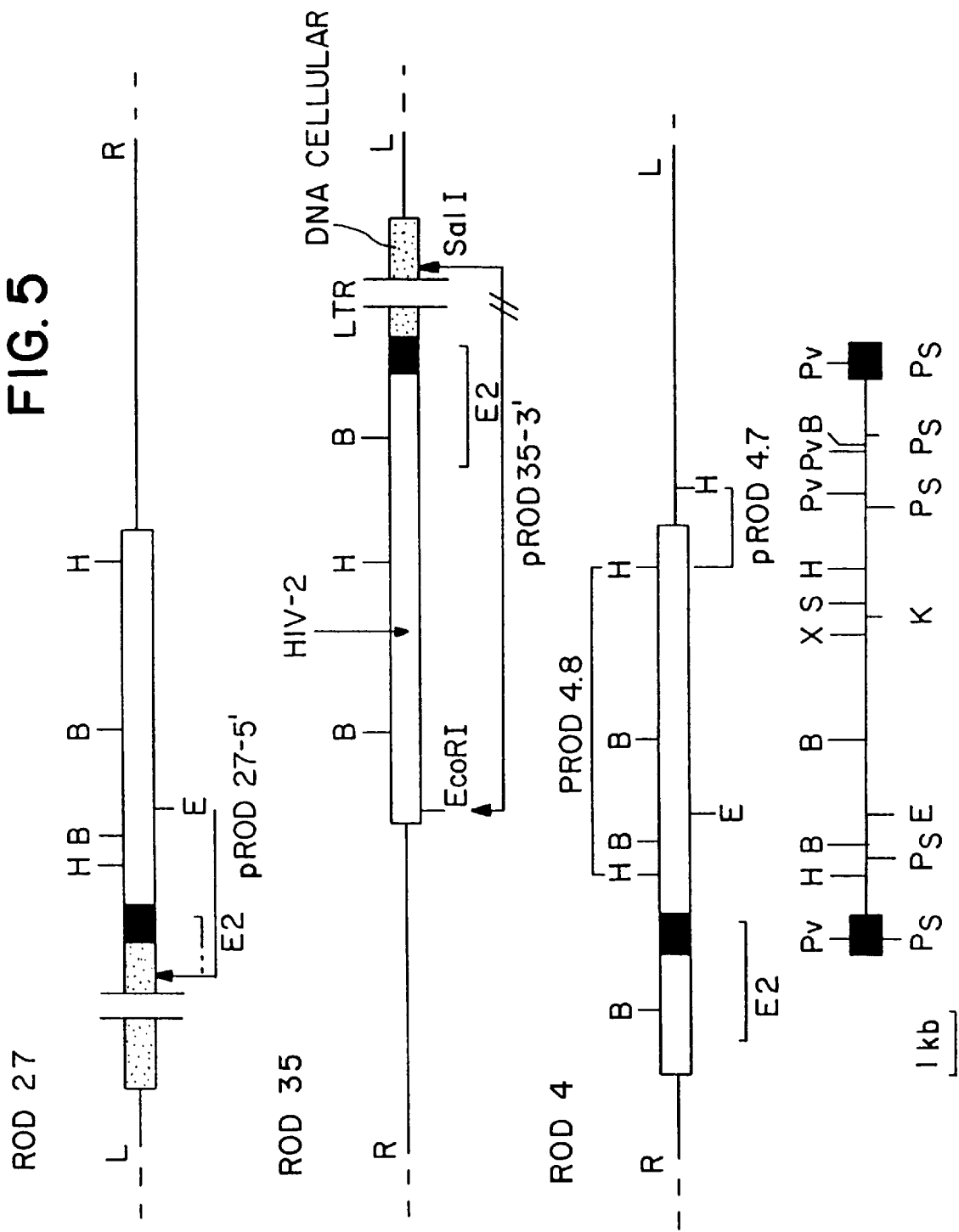

Plasmid pROD 27-5' and pROD 35 in E. coli strain HB 101 are deposited respectively under No. I-626 and I-633 at the CNCM, and have also been deposited at the NCIB (British Collection). These plasmids are depicted in FIG. 5. Plasmids pROD 4–7 and pROD 4–8 in E. coli strain TG1 are deposited respectively under No. I-627 and I-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG.

3B). Even in very low stringency conditions (Tm −42+ C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1B), indicated that HIV-2 is not an envelope variant of HIV-1, as are African isolates from Zaire described by Alizon et al., Cell 40:63–74 (1986).

It was observed that HIV-2 is related more closely to the Simian Immunodeficiency Virus (SIV) than it is to HIV-1. This correlation has been described by F. Clavel et al. in C. R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described in M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

Figure 2D:

In terms of nucleotide sequence, it also appears that HIV-2 is closely related to SIV. The genomic RNA of SIV can be detected in stringent conditions as shown in FIG. 2C by HIV-2 probes corresponding to the LTR and 3' end of the genome (E2) or to the gag or pol genes. Under the same conditions, HIV-1 derived probes do not detect the SIV genome as shown in FIG. 2D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

From an initial survey of the restriction maps for certain of the HIV-2 isolates obtained according to the methods described herein, it is already apparent that HIV-2, like HIV-1, undergoes restriction site polymorphism. FIG. 4A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., Nature 324 (18):691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of λROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides of fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1: Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in *Nature*, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in *Gene*, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques ($10^4$) were screened in situ on replica filters with the 1.5 kb. HindIII fragment from clone J19, corresponding to the 3' part of the genome of the LAV$_{BRU}$ isolate of HIV-1, $^{32}$P labelled to a specific activity of $10^9$ cpm/μg. The filters were prehybridized in 5× SSC, 5× Denhardt solution. 25% formamide, and denatured salmon sperm DNA (100 μg/ml) at 37° C. for 4 hours and hybridized for 16 hours in the same buffer (Tm −42° C.) plus 4×$10^7$ cpm of the labelled probe ($10^6$ cpm/ml. of hybridization buffer). The washing was done in 5× SSC, 0.1% SDS at 25° C. for 2 hours. 20× SSC is 3M NaCl, 0.3M Na citrate. Positive plaques were purified and single-stranded M13 DNA prepared and end-sequenced according to the method described in *Proc. Nat'l. Acad. Sci. USA*, 74: 5463–5467 (1977) of Sanger et al.

Example 2: Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 μg of PstI or undigested, was electrophoresed on a 0.8% agarose gel, and Southern-transferred to nylon membrane. Virion dot-blots were prepared in duplicate, as described by F. Clavel et al. in *Science* 233: 343–346 (1986), specifically incorporated herein by reference, by pelleting volumes of supernatant corresponding to the same amount of reverse transcriptase activity. Prehybridization was done in 50% formamide, 5× SSC, 5× Denhardt solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/μg) for 16 hours at 42° C. Washing was in 0.1× SSC, 0.1% SDS for 2×30 mn. After exposition for 16 hours with intensifying screens, the Southern blot was dehybridized in 0.4N NaOH, neutralized, and rehybridized in the same conditions to the HIV-1 probe labelled to $10^9$ cpm/μg.

Example 3: Cloning in Lambda Phage of the Complete Provirus DNA of HIV-2

DNA from the HIV-2$_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques (2×$10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The λ ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4: Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55 kD and is cleaved into the following proteins:
   a) p 16 (546–950)
   b) p 26 (51–1640)
   c) p 12 (1701–2111)
2) polymerase (1829–4936)
3) Q protein (4869–5513)
4) R protien (5682–5996)
5) X protein (5344–5679)
6) Y protein (5682–5996)
7) Env protein (6147–8720)
8) F protein (8557–9324)
9) TAT gene (5845–6140 and 8307–8400) is expressed by two exons separated by introns.
10) ART protein (6071–6140 and 8307–8536) is similarly the expression product of two exons.
11) LTR:R (1–173 and 9498–9671)
12) U5 (174–299)
13) U3 (8942–9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG

GTAGAGCCTGGGTGTTCCCTGCTAGACTCTCACCAGCACTTGGCCGGTGCTGGGCAGACG
                                     100
GCCCCACGCTTGCTTGCTTAAAAACCTCTTAATAAAGCTGCCAGTTAGAAGCAAGTTAAG

TGTGTGCTCCCATCTCTCCTAGTCGCCGCCTGGTCATTCGGTGTTCACCTGAGTAACAAG
                200
ACCCTGGTCTGTTAGGACCCTTCTTGCTTTGGGAAACCGAGGCAGGAAAATCCCTAGCAG
                                                         300
GTTGGCGCCTGAACAGGGACTTGAAGAAGACTGAGAAGTCTTGGAACACGGCTGACTGAA

GGCAGTAAGGGCGGCAGGAACAAACCACGACGGAGTGCTCCTAGAAAGGCGCGGGCCGAG
```

-continued

```
                              .         .         .         400         .         .
GTACCAAAGGCAGCGTGTGGAGCGGGAGGAGAAGAGGCCTCCGGGTGAAGGTAAGTACCT

ACACCAAAAACTGTAGCCGAAAGGGCTTGCTATCCTACCTTTAGACAGGTAGAAGATTGT
          .         500         .         .         .         .
             MetGlyAlaArgAsnSerValLeuArgGlyLysLysAlaAspGluLeuGluArgIle
GGGAGATGGCGCGAGAAACTCCGTCTTGAGAGGGAAAAAAGCAGATGAATTAGAAAGAA
          .         .         .         .         600         .
      ArgLeuArgProGlyGlyLysLysLysTyrArgLeuLysHisIleValTrpAlaAlaAsn
TCAGGTTACGGCCCGGCGGAAAGAAAAAGTACAGGCTAAAACATATTGTGTGGGCAGCGA

LysLeuAspArgPheGlyLeuAlaGluSerLeuLeuGluSerLysGluGlyCysGlnLys
ATAAATTGGACAGATTCGGATTACCAGAGAGCCTGTTGGAGTCAAAAGAGGGTTGTCAAA
          .         .         .         700         .         .
              IleLeuThrValLeuAspProMetValProThrGlySerGluAsnLeuLysSerLeuPhe
AAATTCTTACAGTTTTAGATCCAATGGTACCGACAGGTTCAGAAAATTTAAAAAGTCTTT

AsnThrValCysValIleTrpCysIleHisAlaGluGluLysValLysAspThrGluGly
TTAATACTGTCTGCGTCATTTGGTGCATACACGCAGAAGAGAAAGTGAAAGATACTGAAG
          .         800         .         .         .         .
          AlaLysGlnIleValArgArgHisLeuValAlaGluThrGlyThrAlaGluLysMetPro
GAGCAAAACAAATAGTGCGGAGACATCTAGTGGCAGAAACAGGAACTGCAGAGAAAATGC
          .         .         .         .         900         .
         SerThrSerArgProThrAlaProSerSerGluLysGlyGlyAsnTyrProValGlnHis
CAAGCACAAGTAGACCAACAGCACCATCTAGCGAGAAGGGAGGAAATTACCCAGTGCAAC

ValGlyGlyAsnTyrThrHisIleProLeuSerProArgThrLeuAsnAlaTrpValLys
ATGTAGGCGGCAACTACACCCATATACCGCTGAGTCCCCGAACCCTAAATGCCTGGGTAA
          .         .         .         1000        .         .
           LeuValGluGluLysLysPheGlyAlaGluValValProGlyPheGlnAlaLeuSerGlu
AATTAGTAGAGGAAAAAAAGTTCGGGGCAGAAGTAGTGCCAGGATTTCAGGCACTCTCAG

GlyCysThrProTyrAspIleAsnGlnMetLeuAsnCysValGlyAspHisGlnAlaAla
AAGGCTGCACGCCCTATGATATCAACCAAATGCTTAATTGTGTGGGCGACCATCAAGCAG
          .         1100        .         .         .         .
            MetGlnIleIleArgGluIleIleAsnGluGluAlaAlaGluTrpAspValGlnLisPro
CCATGCAGATAATCAGGGAGATTATCAATGAGGAAGCAGCAGAATGGGATGTGCAACATC
          .         .         .         .         1200        .
            IleProGlyProLeuProAlaGlyGlnLeuArgGluProArgGlySerAspIleAlaGly
CAATACCAGGCCCCTTACCAGCGGGGCAGCTTAGAGAGCCAAGGGGATCTGACATAGCAG

ThrThrSerThrValGluGluGlnIleGlnTrpMetPheArgProGlnAsnProValPro
CGACAACAAGCACAGTAGAAGAACAGATCCAGTGGATGTTTAGGCCACAAAATCCTGTAC
          .         .         .         1300        .         .
           ValGlyAsnIleTyrArgArgTrpIleGlnIleGlyLeuGlnLysCysValArgMetTyr
CAGTAGGAAACATCTATAGAAGATGGATCCAGATAGGATTGCAGAAGTGTGTCAGGATGT

AsnProThrAsnIleLeuAspIleLysGlnGlyProLysGluProPheGlnSerTyrVal
ACAACCCGACCAACATCCTAGACATAAAACAGGGACCAAAGGAGCCGTTCCAAAGCTATG
          .         .         .         1400        .         .
            AspArgPheTyrLysSerLeuArgAlaGluGlnThrAspProAlaValLysAsnTrpMet
TAGATAGATTCTACAAAAGCTTGAGGGCAGAACAAACAGATCCAGCAGTGAAGAATTGGA
          .         .         .         .         1500        .
          ThrGlnThrLeuLeuValGlnAsnAlaAsnProAspCysLysLeuValLeuLysGlyLeu
TGACCCAAACACTGCTAGTACAAAATGCCAACCCAGACTGTAAATTAGTGCTAAAAGGAC

GlyMetAsnProThrLeuGluGluMetLeuThrAlaCysGlnGlyValGlyGlyProGly
TAGGGATGAACCCTACCTTAGAAGAGATGCTGACCGCCTGTCAGGGGGTAGGTGGGCCAG
          .         .         .         1600        .         .
           GlnLysAlaArgLeuMetAlaGluAlaLeuLysGluValIleGlyProAlaProIlePro
GCCAGAAAGCTAGATTAATGGCAGAGGCCCTGAAAGAGGTCATAGGACCTGCCCCTATCC

PheAlaAlaAlaGlnGlnArgLysAlaPheLysCysTrpAsnCysGlyLysGluGlyHis
CATTCGCAGCAGCCCAGCAGAGAAAGGCATTTAAATGCTGGAACTGTGGAAAGGAAGGGC
          .         1700        .         .         .         .
           SerAlaArgGlnCysArgAlaProArgArgGlnGlyCysTrpLysCysGlyLysProGly
ACTCGGCAAGACAATGCCGAGCACCTAGAAGGCAGGGCTGCTGGAAGTGTGGTAAGCCAG
          .         .         .         .         1800        .
                          ThrGlyArgPhePheArgThrGlyProLeuGly
           HisIleMetThrAsnCysProAspArgGlnAlaGlyPheLeuGlyLeuGlyProTrpGly
GACACATCATGAGAAACTGCCCAGATAGACAGGCAGGTTTTTTAGGACTGGGCCCTTGGG

LysGluAlaProGlnLeuProArgGlyProSerSerAlaGlyAlaAspThrAsnSerThr
         LysLysProArgAsnPheProValAlaGlnValProGlnGlyLeuThrProThrAlaPro
GAAAGAAGCCGCGCAACTTCCCCGTGGCCCAAGTTCCGCAGGGGCTGACACCAACAGCAC
          .         .         .         .         1900        .
           ProSerGlySerSerSerGlySerThrGlyGluIleTyrAlaAlaArgGluLysThrGlu
           ProValAspProAlaValAspLeuLeuGluLysTyrMetGlnGlnGlyLysArgGlnArg
CCCCAGTGGATCCAGCAGTGGATCTACTGGAGAAATATATGCAGCAAGGGAAAAGACAGA
          .         .         .         .         .         .
```

-continued

```
ArgAlaGluArgGluThrIleGlnGlySerAspArgGlyLeuThrAlaProArgAlaGly
  GluGlnArgGluArgProTyrLysGluValThrGluAspLeuLeuHisLeuGluGlnGly
GAGAGCAGAGAGAGACCATACAAGGAAGTGACAGAGGACTTACTGCACCTCGAGCAGG
                .                 .                 2000
   GlyAspThrIleGlnGlyAlaThrAsnArgGlyLeuAlaAlaProGlnPheSerLeuTrp
     GluThrProTyrArgGluProProThrGluAspLeuLeuHisLeuAsnSerLeuPheGly
GGGAGACACCATACAGGGAGCCACCAACAGAGGACTTGCTGCACCTCAATTCTCTCTTTG
       .                 .                 .                 2100
   LysArgProValValThrAlaTyrIleGluGlyGlnProValGluValLeuLeuAspThr
     LysAspGln
GAAAAGACCAGTAGTCACAGCATACATTGAGGGTCAGCCAGTAGAAGTCTTGTTAGACAC

GlyAlaAspAspSerIleValAlaGlyIleGluLeuGlyAsnAsnTyrSerProLysIle
AGGGGCTGACGACTCAATAGTAGCAGGAATAGAGTTAGGGAACAATTATAGCCCAAAAAT
            .                 .                 2200         .
  ValGlyIleGlyGlyPheIleAsnThrLysGluTyrLysAsnValGluIleGluVal
AGTAGGGGGAATAGGGGGATTCATAAATACCAAGGAATATAAAAATGTAGAAATAGAAGT
       .                 .                 .                 .
    LeuAsnLysLysValArgAlaThrIleMetThrGlyAspThrProIleAsnIlePheGly
TCTAAATAAAAAGGTACGGGCCACCATAATGACAGGCGACACCCCAATCAACATTTTTGG
      .                 .                 2300              .
     ArgAsnIleLeuThrAlaLeuGlyMetSerLeuAsnLeuProValAlaLysValGluPro
CAGAAATATTCTGACAGCCTTAGGCATGTCATTAAATCTACCAGTCGCCAAAGTAGAGCC
       .                .                 .                 2400
     IleLysIleMetLeuLysProGlyLysAspGlyProLysLeuArgGlnTrpProLeuThr
AATAAAAATAATGCTAAAGCCAGGGAAAGATGGACCAAAACTGAGACAATGGCCCTTAAC
          .                .                 .                 .
     LysGluLysIleGluAlaLeuLysGluIleCysGluLysMetGluLysGluGlyGlnLeu
AAAAGAAAAAATAGAAGCACTAAAAGAAATCTGTGAAAAAATGGAAAAAGAAGGCCAGCT
        .                 .                 2500              .
    GluGluAlaProProThrAsnProTyrAsnThrProThrPheAlaIleLysLysLysAsp
AGAGGAAGCACCTCCAACTAATCCTTATAATACCCCCACATTTGCAATCAAGAAAAAGGA
         .                .                 .                 .
    LysAsnLysTrpArgMetLeuIleAspPheArgGluLeuAsnLysValThrGlnAspPhe
CAAAAACAAATGGAGGATGCTAATAGATTTCAGAGAACTAAACAAGGTAACTCAAGATTT
      .                 2600             .                 .
    ThrGluIleGlnLeuGlyIleProHisProAlaGlyLeuAlaLysLysArgArgIleThr
CACAGAAATTCAGTTAGGAATTCCACACCCAGCAGGGTTGGCCAAGAAGAGAAGAATTAC
       .                .                 .                 2700
   ValLeuAspValGlyAspAlaTyrPheSerIleProLeuHisGluAspPheAtgProTyr
TGTACTAGATGTAGGGGATGCTTACTTTTCCATACCACTACATGAGGACTTTAGACCATA
         .                 .                 .                 .
    ThrAlaPheThrLeuProSerValAsnAsnAlaGluProGlyLysArgTyrIleTyrLys
TACTGCATTTACTCTACCATCAGTGAACAATGCAGAACCAGGAAAAAGATACATATATAA
            .                 .                 2800             .
    ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT
       .                 .                 .                 .
    LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
        .                 2900              .                .
    LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
        .                 .                 .                 3000
    LeuLeuAsnGlyLeuGlyPheSerThrProAsoGluLysPheGlnLysAspProProTyr
ACTTCTAAATGGCCTAGGATTTTCTACCCCAGATGAGAAGTTCCAAAAAGACCCTCCATA
        .                 .                 .                 .
    HisTrpMetGlyTyrGluLeuTrpProThrLysTrpLeuGlnLysIleGlnLeuPro
CCACTGGATGGGCTATGAACTATGGCCAACTAAATGGAAGTTGCAGAAAATACAGTTGCC
          .                 .                 3100              .
    GlnLysGluIleTrpThrValAsnAspIleGlnLysLeuValGlyValLeuAsnTrpAla
CCAAAAAGAAATATGGACAGTCAATGACATCCAGAAGCTAGTGGGTGTCCTAAATTGGGC
        .                 .                 .                 .
    AlaGlnLeuTyrProGlyIleLysThrLysHisLeuCysArgLeuIleArgGlyLysMet
AGCACAACTCTACCCAGGGATAAAGACCAAACACTTATGTAGGTTAATCAGAGGAAAAAT
        .                 3200             .                 .
    ThrLeuThrGluGluValGlnTrpThrGluLeuAlaGluAlaGluLeuGluGluAsnArg
GACACTCACAGAAGAAGTACAGTGGACAGAATTACCAGAAGCAGAGCTAGAAGAAAACAG
        .                 .                 .                 3300
    IleIleLeuSerGlnGluGlnGlyHisTyrTyrGlnGluGluLysGluLeuGluAla
AATTATCCTAAGCCAGGAACAAGAGGGACACTATTACCAAGAAGAAAAAGAGCTAGAAGC
         .                 .                 .                 .
    ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
         .                 .                 3400              .
    LeuLysValGlyLysTyrAlaLysValLysAsnThrHisThrAsnGlyIleArgLeuLeu
TCTAAAAGTAGGAAAATATGCAAAGGTGAAAAACACCCCATACCAATGGAATCAGATTGTT
        .                 .                 .                 .
    AlaGlnValValGlnLysIleGlyLysGluAlaLeuValIleTrpGlyArgIleProLys
AGCACAGGTAGTTCAGAAAATAGGAAAAGAAGCACTAGTCATTTGGGGACCAATACCAAA
```

-continued

```
                         .          .         .         .
              3500       .          .         .         .
  PheHisLeuProValGluArgGluIleTrpGluGlnTrpTrpAspAsnTyrTrpGlnVal
  ATTTCACCTACCAGTAGAGAGAGAAATCTGGGAGCAGTGGTGGGATAACTACTGGCAAGT
           .       .       .        3600      .         .
    ThrTrpIleProAspTrpAspPheValSerThrProProLeuValArgLeuAlaPheAsn
  GACATGGATCCCAGACTGGGACTTCGTGTCTACCCCACCACTGGTCAGGTTAGCGTTTAA
           .         .         .       .         .         .
  LeuValGlyAspProIleProGlyAlaGluThrPheTyrThrAspGlySerCysAsnArg
  CCTGGTAGGGGATCCTATACCAGGTGCAGAGACCTTCTACACAGATCGATCCTGCAATAG
           .         .         .         3700      .         .
    GlnSerLysGluGlyLysAlaGlyTyrValThrAspArgGlyLysAspLysValLysLys
  GCAATCAAAAGAAGGAAAAGCAGGATATGTAACAGATAGAGGGAAAGACAAGGTAAAGAA
           .         .         .         .         .         .
    LeuGluGlnThrThrAsnGlnGlnAlaGluLeuGluAlaPheAlaMetAlaLeyThrAsp
  ACTAGAGCAAACTACCAATCAGCAAGCAGAACTAGAAGCCTTTGCGATGGCACTAACAGA
           .         3800      .         .         .         .
    SerGlyProLysValAsnIleIleValAspSerGlnTyrValMetGlyIleSerAlaSer
  CTCGGGTCCAAAAGTTAATATTATAGTAGACTCACAGTATGTAATGGGGATCAGTGCAAG
           .         .         .         3900      .         .
    GlnProThrGluSerGluSerLysIleValAsnGlnIleIleGluMetIleLysLys
  CCAACCAACAGAGTCAGAAAGTAAAATAGTGAACCAGATCATAGAAGAAATGATAAAAAA
           .         .         .         .         .         .
    GluAlaIleTyrValAlaTrpValProAlaHisLysGlyIleGlyGlyAsnGlnGluVal
  GGAAGCAATCTATGTTGCATGGGTCCCAGCCCACAAAGGCATAGGGGGAAACCAGGAAGT
           .         .         .         4000      .         .
    AspHisLeuValSerGlnGlyIleArgGlnValLeuPheLeuGluLysIleGluProAla
  AGATCATTTAGTGAGTCAGGGTATCAGACAAGTGTTGTTCCTGGAAAAAATAGAGCCCGC
           .         .         .         .         .         .
    GlnGluHisGluLysTyrHisSerAsnValLysGluLeuSerHisLysPheGlyIle
  TCAGGAAGAACATGAAAAATATCATAGCAATGTAAAAGAACTGTCTCATAAATTTGGAAT
           .         4100      .         .         .         .
    ProAsnLeuValAlaArgGlnIleValAsnSerCysAlaGlnCysGlnGlnLysGlyGlu
  ACCCAATTTAGTGGCAAGGCAAATAGTAAACTCATGTGCCCAATGTCAACAGAAAGGGGA
           .         .         .         .         .         4200
    AlaIleHisGlyGlnValAsnAlaGluLeuGlyTheTrpGlnMetAspCysThrHisLeu
  AGCTATACATGGGCAAGTAAATGCAGAACTAGCCACTTGGCAAATGGACTGCACACATTT
           .         .         .         .         .         .
    GluGlyLysIleIleIleValAlaValHisValAlaSerGlyPheIleGluAlaGluVal
  AGAAGGAAAGATCATTATAGTAGCAGTACATGTTGCAAGTGGATTTATAGAAGCAGAAGT
           .         .         .         4300      .         .
    IleProGlnGluSerGlyArgGlnThrAlaLeuPheLeuLeuLysLeuAlaSerArgTrp
  CATCGCACAGGAATCAGGAAGACAAACAGCACTCTTCCTATTGAAACTGGCAAGTAGGTG
           .         .         .         .         .         .
    ProIleThrHisLeuHisThrAspAsnGlyAlaAsnPheThrSerGlnGluValLysMet
  GCCAATAACACACTTGCATACAGATAATGGTGCCAACTTCACTTCACAGGAGGTGAAGAT
           .         4400      .         .         .         .
    ValAlaTrpTrpIleGluIleGluGlnSerPheGlyValProTyrAsnProGlnSerGln
  GGTAGCATGGTGGATAGGTATAGAACAATCCTTTGGAGTACCTTACAATCCACAGAGCCA
           .         .         .         .         .         4500
    GlyValValGluAlaMetAsnHisHisLeuLysAsnGluIleSerArgIleArgGluGln
  AGGAGTAGTAGAAGCAATGAATCACCATCTAAAAAACCAAATAAGTAGAATCAGAGAACA
           .         .         .         .         .         .
    AlaAsnThrIleGluThrIleValLeuMetAlaIleHisCysMetAsnPheLysArgArg
  GGCAAATACAATAGAAACAATAGTACTAATGGCAATTCATTGCATGAATTTTAAAAGAAG
           .         .         .         4600      .         .
    GlyGluIleGlyAspMetThrProSerGluArgLeuIleAsnMetIleThrThrGluGln
  GGGGGGAATAGGGGATATGACTCCATCAGAAAGATTAATCAATATGATCACCACAGAACA
           .         .         .         .         .         .
    GluIleGlnPheLeuGlnAlaLysAsnSerLysLeuLysAspPheArgValTyrPheArg
  AGAGATACAATTCCTCCAAGCCAAAAATTCAAAATTAAAAGATTTTCGGGTCTATTTCAG
           .         4700      .         .         .         .
    GluGlyArgAspGlnLeuTrpLysGlyProGlyGluLeuLeuTrpLysGlyGluGlyAla
  AGAAGGCAGACATCAGTTGTGGAAAGGACCTGGGGAACTACTGTGGAAAGGAGAAGGAGC
           .         .         .         .         .         4800
    ValLeuValLysValGlyThrAspIleLysIleIleProArgArgLysAlaLysIleIle
  AGTCCTAGTCAAGGTAGGAACAGACATAAAAATAATACCAAGAAGGAAAGCCAAGATCAT
           .         .         .         .         .         .
    AspAspTyrGlyGlyArgGlnGluMetAspSerGlySerHisLeuGluGlyAlaArgGlu
         MetGluGluAspLysArgTrpIleValValProThrTrpArgValProGlyArg
  CAGACACTATGGAGGAAGACAAGAGATGGATAGTGGTTCCCACCTGGAGGGTGCCAGGGA
           .         .         .         4900      .         .
  AspGlyGluMetAla
    MetGluLysTrpHisSerLeuValLysTyrLeuLysTyrLysThrLysAspLeuGluLys
  GGATGGAGAAATGGCATAGCCTTGTCAAGTATCTAAAATACAAAACAAAGGATCTAGAAA
           .         .         .         .         .         .
     ValCysTyrValProHisHisLysValGlyTrpAlaTrpTrpThrCysSerArgValIle
  AGGTGTGCTATGTTCCCCACCATAAGGTGGGATGGGCATGGTGGACTTGCAGCAGGGTAA
           .         5000      .         .         .         .
    PheProLeuLysGlyAsnSerHisLeuGluIleGlnAlaTyrTrpAsnLeuThrProGlu
  TATTCCCATTAAAAGGAAACAGTCATCTAGAGATACAGGCATATTGGAACTTAACACCAG
```

```
                                              .            .            5100
          LysGlyTrpLeuSerSerTyrSerValArgIleThrTrpTyrThrGluLysPheTrpThr
          AAAAAGGATGGCTCTCCTCTTATTCAGTAAGAATAACTTGGTACACAGAAAAGTTCTGGA

AspValThrProAspCysAlaAspValLeuIleHisSerThrTyrPheProCysPheThr
             CAGATGTTACCCCAGACTGTGCAGATGTCCTAATACATAGCACTTATTTCCCTTGCTTTA
                              .            .   5200       .            .
             AlaGlyGluValArgAlaIleArgGlyGluLysLeuLeuSerCysCysAsnTyrPro
             CAGCAGGTGAAGTAAGAAGAGCCATCAGAGGGGAAAAGTTATTGTCCTGCTGCAATTATC

ArgAlaHisArgAlaGlnValProSerLeuGlnPheLeuAlaLeuValValValGlnGln
          CCCGAGCTCATAGACCCCAGGTACCGTCACTTCAATTTCTGGCCTTAGTGGTAGTCCAAC
                           .         5300        .            .
             MetThrAspProArgGluThrValProProGlyAsnSerGlyGluGluThrIleGly
             AsnAspArgProGlnArgAspSerThrThrArgLysGlnArgArgArgAspTyrArgArg
             AAAATGACAGACCCCAGAGAGACAGTACCACCAGGAAACAGCGGCGAAGAGACTATCGGA
                                                  .            .   5400
          GluAlaPheAlaTrpLeuAsnArgThrValGluAlaIleAsnArgGluAlaValAsnHis
             GlyLeuArgLeuAlaLysGlnAspSerArgSerHisLysGlnArgSerSerGluSerPro
          GAGGCCTTCGCCTGGCTAAACAGGACAGTAGAAGCCATAAACAGAGAAGCAGTGAATCAC

LeuProArgGluLeuIlePheGlnValTrpGlnArgSerTrpArgTyrTrpHisAspGlu
             ThrProArgThrTyrPheProGlyValAlaGluValLeuGluIleLeuAla
          CTACCCCGAGAACTTATTTTCCAGGTGTGGCAGAGGTCCTGGAGATACTGGCATGATGAA
                      .           .          5500        .             .
          GluGlyMetSerGluSerTyrThrLysTyrArgTyrLeuCysIleIleGlnLysAlaVal
          CAAGGGATGTCAGAAAGTTACACAAAGTATAGATATTTGTGCATAATACAGAAAGCAGTG

TyrMetHisValArgLysGlyCysThrCysLeuGlyArgGlyHisGlyProGlyGlyTrp
          TACATGCATGTTAGGAAAGGGTGTACTTGCCTGGGGAGGGGACATGGGCCAGGAGGGTGG
                      .    5600         .            .           .
          ArgProGlyProProProProProProProGlyLeuVal
                                                     MetAlaGluAlaProThrGlu
          AGACCAGGGCCTCCTCCTCCTCCCCCTCCAGGTCTGGTCTAATGGCTGAAGCACCAACAG
                    .            .           .            .         5700
               LeuProProCalAspGlyThrProLeuArgGluProGlyAspGluTrpIleIleGluIle
               AGCTCCCCCCGGTGGATGGGACCCCACTGAGGGAGCCAGGGGATGAGTGGATAATAGAAA
                                                    .            .
               LeuArgGluIleLysGluGluAlaLeuLysHisPheAspProArgLeuLeuIleAlaLeu
               TCTTGAGAGAAATAAAAGAAGAAGCTTTAAAGCATTTTGACCCTCGCTTGCTAATTGCGC
                       .          .            .   5800      .             .
                                       MetGluThrProLeuLysAlaProGluSerSerLeu
             GlyLysTyrIleTyrThrArgHisGlyAspThrLeuGluGlyAlaArgGluLeuIleLys
             TTGGCAAATATATCTATACTAGACATGGAGACACCCTTGAAGGCGCCAGAGAGCTCATTA

LysSerCysAsnGluProPheSerArgThrSerGluGlnAspValAlaThrGlnGluLeu
             ValLeuGlnArgAlaLeuPheThrHisPheArgAlaGlyCysGlyHisSerArgIleGly
          AAGTCCTGCAACGAGCCCTTTTCACGCACTTCAGAGCAGGATGTGGCCACTCAAGAATTG
                           .          5900       .             .          .
          AlaAtgGlnGlyGluGluIleLeuSerGlnLeuTyrArgProLeuGluThrCysAsnAsn
             GlnThrArgGlyGlyAsnProLeuSerAlaIleProThrProArgAsnMetGln
          GCCAGACAAGGGGAGGAAATCCTCTCTCAGCTATACCGACCCCTAGAAACATGCAATAAC
                   .            .          .             .          6000
          SerCysTyrCysLysArgCysCysTyrHisCysGlnMetCysPheLeuAsnLysGlyLeu
          TCATGCTATTGTAAGCGATGCTGCTACCATTGTCAGATGTGTTTTCTAAACAAGGGGCTC

GlyIleCysTyrGluArgLysGlyArgArgArgThrProLysLysThrLysThrHis
                    MetAsnGluArgAlaAspGluGluGlyLeuGlnArgLysLeuArgLeuIle
          GGGATATGTTATGAACGAAAGGGCAGACGAAGAAGGACTCCAAAGAAAACTAAGACTCAT
                   .           .           6100      .              .
          ProSerProThrProAspLys
           ArgLeuLeuHisGlnThr
                                     MetMetAsnGlnLeuLeuIleAlaIleLeuLeuAla
          CCGTCTCCTACACCAGACAAGTGAGTATGATGAATCAGCTGCTTATTGCCATTTTATTAG

SerAlaCysLeuValTyrCysThrGlnTyrValThrValPheTyrGlyValProThrTrp
             CTAGTGCTTGCTTAGTATATTGCACCCAATATGTAACTGTTTTCTATGGCGTACCCACGT
                             .          6200         .           .
             LysAsnAlaThrIleProLeuPheCysAlaThrArgAsnArgAspThrTrpGlyThrIle
             GGAAAAATGCAACCATTCCCCTCTTTTGTGCAACCAGAAATAGGGATACTTGGGGAACCA
                      .            .           .             .     6300
             GlnCysLeuProAspAsnAspAspTyrGlnGluIleThrLeuAsnValThrGluAlaPhe
             TACAGTGCTTGCCTGACAATGATGATTATCAGGAAATAACTTTGAATGTAACAGAGCCTT

AspAlaTrpAsnAsnThrValThrGluGlnAlaIleGluAspValTrpHisLeuPheGlu
             TTGATGCATGGAATAATACAGTAACAGAACAAGCAATAGAAGATGTCTGGCATCTATTCG
                           .          .             .    6400     .            .
               ThrSerIleLysProCysValLysLeuThrProLeuCysValAlaMetLysCysSerSer
               AGACATCAATAAAACCATGTGTCAAACTAACACCTTTATGTGTAGCAATGAAATGCAGCA
```

```
                         -continued
      ThrGluSerSerThrGluAsnAsnThrThrSerLysSerThrSerThrThrThrThrThr
      GCACAGAGAGCAGCACAGGGAACAACACAACCTCAAAGAGCACAAGCACAACCACAACCA
                .         6500        .         .         .
          ProThrAspGlnGluGlnGluIleSerGluAspThrProCysAlaArgAlaAspAsnCys
      CACCCACAGACCAGGAGCAAGAGATAAGTGAGGATACTCCATGCGCACGCGCAGACAACT
                .         .         .         .         6600
        SerGlyLeuGlyGluGluThrIleAsnCysGlnPheAsnMetThrGlyLeuGluArg
      GCTCAGGATTGGGAGAGGAAGAAACGATCAATTGCCAGTTCAATATGACAGGATTAGAAA
                .         .         .         .         .

AspLysLysLysGlnTyrAsnGluThrTrpTyrSerLysAspValValCysGluThrAsn
      GAGATAAGAAAAAACAGTATAATGAAACATGGTACTCAAAAGATGTGGTTTGTGAGACAA
                .         .         .         6700        .
        AsnSerThrAsnGlnThrGlnCysTyrMetAsnHisCysAsnThrSerValIleThrGlu
      ATAATAGCACAAATCAGACCCAGTGTTACATGAACCATTGCAACACATCAGTCATCACAG
                .         .         .         .         .

SerCysAspLysHisTyrTrpAspAlaIleArgPheArgTyrCysAlaProProGlyTyr
      AATCATGTGACAAGCACTATTGGGATGCTATAAGGTTTAGATACTGTGCACCACCGGGTT
                .         6800        .         .         .
        AlaLeuLeuArgCysAsnAspThrAsnTyrSerGlyPheAlaProAsnCysSerLysVal
      ATGCCCTATTAAGATGTAATGATACCAATTATTCAGGCTTTGCACCCAACTGTTCTAAAG
                .         .         .         .         6900
        ValAlaSerThrCysThrArgMetMetGluThrGlnThrSerThrTrpPheGlyPheAsn
      TAGTAGCTTCTACATGCACCAGGATGATGGAAACGCAAACTTCCACATGGTTTGGCTTTA
                .         .         .         .         .

GlyThrArgAlaGluAsnArgThrTyrIleTyrTrpHisGlyArgAspAsnArgThrIle
      ATGGCACTAGAGCAGAGAATAGAACATATATCTATTGGCATGGCAGAGATAATAGAACTA
                .         .         .         7000        .
       IleSerLeuAsnLysTyrTyrAsnLeuSerLeuHisCysLysArgProGlyAsnLysThr
      TCATCAGCTTAAACAAATATTATAATCTCAGTTTGCATTGTAAGAGGCCAGGGAATAAGA
                .         .         .         .         .

ValLysGlnIleMetLeuMetSerGlyHisValPheHisSerHisTyrGlnProIleAsn
      CAGTGAAACAAATAATGCTTATGTCAGGACATGTGTTTCACTCCCACTACCAGCCGATCA
                .         7100        .         .         .
       LysArgProArgGlnAlaTrpCysTrpPheLysGlyLysTrpLysAspAlaMetGlnGlu
      ATAAAAGACCCAGACAAGCATGGTGCTGGTTCAAAGGCAAATGGAAAGACGCCATGCAGG
                .         .         .         .         7200
       ValLysGluThrLeuAlaLysHisProArgTyrArgGlyThrAsnAspThrArgAsnIle
      AGGTGAAGGAAACCCTTGCAAAACATCCCAGGTATAGAGGAACCAATGACACAAGGAATA
                .         .         .         .         .

SerPheAlaAlaProGlyLysGlySerAspProGluValAlaTyrMetTrpThrAsnCys
      TTAGCTTTGCAGCGCCAGGAAAAGGCTCAGACCCAGAAGTAGCATACATGTGGACTAACT
                .         .         .         7300        .
       ArgGlyGluPheLeuTyrCysAsnMetThrTrpPheLeuAsnTrpIleGluAsnLysThr
      GCAGAGGAGAGTTTCTCTACTGCAACATGACTTGGTTCCTCAATTGGATAGAGAATAAGA
                .         .         .         .         .

HisArgAsnTyrAlaProCysHisIleLysGlnIleIleAsnThrTrpHisLysValGly
      CACACCGCAATTATGCACCGTGCCATATAAAGCAAATAATTAACACATGGCATAAGGTAG
                .         7400        .         .         .
       ArgAsnValTyrLeuProProArgGluGlyGluLeuSerCysAsnSerThrValThrSer
      GGAGAAATGTATATTTGCCTCCCAGGGAAGGGGAGCTGTCCTGCAACTCAACAGTAACCA
                .         .         .         .         7500
       IleIleAlaAsnIleAspTrpGlnAsnAsnAsnGlnThrAsnIleThrPheSerAlaGlu
      GCATAATTGCTAACATTGACTGGCAAAACAATAATCAGACAAACATTACCTTTAGTGCAG
                .         .         .         .         .

ValAlaGluLeuTyrArgLeuGluLeuGlyAspTyrLysLeuValGluIleThrProIle
      AGGTGGCAGAACTATACAGATTGGAGTTGGGAGATTATAAATTGGTAGAAATAACACCAA
                .         .         .         7600        .
       GlyPheAlaProThrLysGluLysArgTyrSerSerAlaHisGlyArgHisThrArgGly
      TTGGCTTCGCACCTACAAAAGAAAAAAGATACTCCTCTGCTCACGGGAGACATACAAGAG
                .         .         .         .         .

ValPheValLeuGlyPheLeuGlyPheLeuAlaThrAlaGlySerAlaMetGlyAlaAla
      GTGTTCGTGCTAGGGTTCTTGGGTTTTCTCGCAACAGCAGGTTCTGCAATGGGCGCGG
                .         7700        .         .         .
       SerLeuThrValSerAlaGlnSerArgThrLeuLeuAlaGlyIleValGlnGlnGlnGln
      CGTCCCTGACCGTGTCGGCTCAGTCCCGGACTTTACTGGCCGGGATAGTGCAGCAACAGC
                .         .         .         .         7800
       GlnLeuLeuAspValValLysArgGlnGlnGluLeuLeuArgLeuThrValTrpGlyThr
      AACAGCTGTTGGACGTGGTCAAGAGACAACAAGAACTGTTGCGACTGACCGTCTGGGGAA
                .         .         .         .         .

LysAsnLeuGlnAlaAlaValThrAlaIleGluLysTyrLeuGlnAspGlnAlaArgLeu
      CGAAAAACCTCCAGGCAACAGTCACTGCTATAGAGAAGTACCTACAGGACCAGGCGCGGC
                .         .         .         7900        .
       AsnSerTrpGlyCysAlaPheArgGlnValCysHisThrThrValProTrpValAsnAsp
      TAAATTCATGGGGATGTGCGTTTAGACAAGTCTGCCACACTACTGTACCATGGGTTAATG
                .         .         .         .         .

SerLeuAlaProAspTrpAspAsnMetThrTrpGlnGluTrpGluLysGlnValArgTyr
      ATTCCTTAGCACCTGACTGGGACAATATGACGTGGCAGGAATGGGAAAAACAAGTCCGCT
                .         8000        .         .         .
       LeuGluAlaAsnIleSerLysSerLeuGluGlnAlaGlnIleGlnGlnGluLysAsnMet
      ACCTGGAGGCAAATATCAGTAAAAGTTTAGAACAGGCACAAATTCAGCAAGAGAAAAATA
```

-continued

```
                                                   8100
  TyrGluLeuGlnLysLeuAsnSerTrpAspIlePheGlyAsnTrpPheAspLeuThrSer
TGTATGAACTACAAAAATTAAATAGCTGGGATATTTTTGGCAATTGGTTTGACTTAACCT

TrpValLysTyrIleGlnTyrGlyValLeuIleIleValAlaValIleAlaLeuArgIle
CCTGGGTCAAGTATATTCAATATGGAGTCCTTATAATAGTAGCAGTAATAGCTTTAACAA
                              8200
  ValIleTyrValValGlnMetLeuSerArgLeuArgLysGlyTyrArgProValPheSer
TAGTGATATATGTAGTACAAATGTTAAGTAGGCTTAGAAAGGGCTATAGGCCTGTTTTCT

SerIleSerThrArgThrGlyAspSerGlnPro
                       AsnProTyrProGlnGlyProGlyThrAlaSerGln
  SerProProGlyTyrIleGlnGlnIleHisIleHisLysAspArgGlyGlnProAlaAsn
CTTCCCCCCCCGGTTATATCCAACAGATCCATATCCACAAGGACCGGGGACAGCCAGCCA
              8300
ThrLysLysGlnLysLysThrValGluAlaThrValGluThrAspThrGlyProGlyArg
  ArgArgAsnArgArgArgArgTrpLysGlnArgTrpArgGlnIleLeuAlaLeuAlaAsp
   GluGluThrGluGluAspGlyGlySerAsnGlyGlyAspArgTyrTrpProTrpProIle
ACGAAGAAACAGAAGAAGACGGTGGAAGCAACGGTGGAGACAGATACTGGCCCTGGCCGA
                                                  8400
  SerIleTyrThrPheProAspProProAlaAspSerProLeuAspGlnThrIleGlnHis
    AlaTyrIleHisPheLeuIleArgGlnLeuIleArgLeuLeuThrArgLeuTyrSerIle
TAGCATATATACATTTCCTGATCCGCCAGCTGATTCGCCTCTTGACCAGACTATACAGCA

LeuGlnGlyLeuThrIleGlnGluLeuProAspProProThrHisLeuProGluSerGln
    CysArgAspLeuLeuSerArgSerPheLeuThrLeuGlnLeuIleTyrGlnAsnLeuArg
TCTGCAGGGACTTACTATCCAGGAGCTTCCTGACCCTCCAACTCATCTACCAGAATCTCA
                              8500
  ArgLeuAlaGluThr                MetGlyAlaSerGlySerLysLys
    AspTrpLeuArgLeuArgThrAlaPheLeuIleTyrGlyCysGluTrpIleGlnGluAla
GAGACTGGCTGAGACTTAGAACAGCCTTCTTGCAATATGGGTGCGAGTGGATCCAAGAAG

HisSerArgProProArgGlyLeuGlnGluArgLeuLeuArgAlaArgAlaGlyAlaCys
   PheGlnAlaAlaAlaArgAlaThrArgGluThrLeuAlaGlyAlaCysArgGlyLeuTrp
CATTCCAGGCCGCCGCGAGGGCTACAAGAGAGACTCTTGAGGGCGCGTGCAGGGGCTTCT
            8600
GLyGlyTyrTrpAsnGluSerGlyGluGluTyrSerArgPheGlnGluGlySerAspArg
   ArgValLeuGluArgIleGlyArgGlyIleGluAlaValProArgArgIleArgGlnGly
GCAGCGTATTGGAACGAATCGGGAGGGGAATACTCGCGGTTCCAAGAAGGATCAGACAGC
                                                 8700
GluGlnLysSerProSerCysGluGlyArgGlnTyrGlnGlnGlyAspPheMetAsnThr
    AlaGluIleAlaLeuLeu
GAGCAGAAATCGCCCTCCTGTGAGGGACGGCAGTATCAGCAGGGAGACTTTATGAATACT

PRoTrpLysAspProAlaAlaGluArgGluLysAsnLeuTyrArgGlnGlnAsnMetAsp
CCATGGAAGGACCCAGCAGCAGAAAGGGAGAAAAATTTGTACAGGCAACAAAATATGGAT
                                        8800
AspValAspSerAspAspAspAspGlnValArgValSerValThrProLysValProLeu
GATGTAGATTCAGATGATGATGACCAAGTAAGAGTTTCTGTCACACCAAAAGTACCACTA

ArgProMetThrHisArgLeuAlaIleAspMetSerHisLeuIleLysThrArgGlyGly
AGACCAATGACACATAGATTGGCAATAGATATGTCACATTTAATAAAAACAAGGGGGGGA
           8900
LeuGluGlyMetPheTyrSerGluArgArgHisLysIleLeuAsnIleTyrLeuGluLys
CTGGAAGGGATGTTTTACAGTGAAAGAAGACATAAAATCTTAAATATATACTTAGAAAAG
                                              9000
GluGluGlyIleIleAlaAspTrpGlnAsnTyrThrHisGlyProGlyValArgTyrPro
CAAGAAGGGATAATTGCAGATTGGCAGAACTACACTCATGGGCCAGGAGTAAGATACCCA

MetPhePheGlyTrpLeuTrpLysLeuValProValAspValProGlnGluGlyGluAsp
ATGTTCTTTGGGTGGCTATGGAAGCTAGTACCAGTAGATGTCCCACAAGAAGGGGAGGAC
                                9100
ThrGluThrHisCysLeuValHisProAlaGlnThrSerLysPheAspAspProHisGly
ACTGAGACTCACTGCTTAGTACATCCAGCACAAACAAGCAAGTTTGATGACCCGCATGGG

GluThrLeuValTrpGluPheAspProLeuLeuAlaTyrSerTyrGluAlaPheIleArg
GAGACACTAGTCTGGGAGTTTGATCCCTTGCTGGCTTATAGTTACGAGGCTTTTATTCGG
            9200
TyrProGluGluPheGlyHisLysSerGlyLeuProGluGluGluTrpLysAlaArgLeu
TACCCAGAGGAATTTGGGCACAAGTCAGGCCTGCCAGAGGAAGAGTGGAAGGCGAGACTG
                                             9300
LysAlaArgGlyIleProPheSer
AAAGCAAGAGCAATACCATTTAGTTAAAGACAGGAACAGCTATACTTGGTCAGGGCAGGA

AGTAACTAACAGAAACAGCTGAGACTGCAGGGACTTTCCAGAAGGGGCTGTAACCAAGGG
                              9400
AGGGACATGGAGGAGCTGGTGGGAACGCCCTCATATTCTCTGTATAAATATACCCGCT

AGCTTGCATTGTACTTCGGTCGCTCTGCGGAGAGGCTGGCAGATTGAGCCCTGGGAGGTT
           9500
```

-continued
```
CTCTCCAGCAGTAGCAGGTAGAGCCTGGGTGTTCCCTGCTAGACTCTCACCAGCACTTGG
    .         .         .         .         .         .
                                                          9600
CCGGTGCTGGGCAGACGGCCCCACGCTTGCTTGCTTAAAAACCTCCTTAATAAAGCTGCC
    .         .         .         .         .         .

AGTTAGAAGCA
    .
```

Example 5: Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

Envelope sequence

```
MetMetAsnGlnLeuLeuIleAlaIleLeuLeuAlaSeraLACys
ATGATGATCCAGCTGCTTATTGCCATTTTATTAGCTAGTGCTTGC
         .         .         .         .
LeuValTyrCysThrGlnTyrValThrValPheTyrGlyValPro
TTAGTATATTGCACCCAATATGTAACTGTTTTCTATGGCGTACCC
    .         .         .         .         .
ThrTrpLysAsnAlaThrIleProLeuPheCysAlaThrArgAsn
ACGTGGAAAAATGCAACCATTCCCCTGTTTTGTGCAACCAGAAAT
       100         .         .         .
ArgAspThrTrpGlyThrIleGlnCysLeuProAspAsnAspAsp
AGGGATACTTGGGGAACCATACAGTGCTTGCCTGACAATGATGAT
    .         .         .         .         .
TyrGlnGluIleThrLeuAsnValThrGluAlaPheAspAlaTrp
TATCAGGAAATAACTTTGAATGTAACAGAGGCTTTTGATGCATGG
         .        200          .         .
AsnAsnThrValThrGluGlnAlaIleGluAspValTrpHisLeu
AATAATACAGTAACAGAACAAGCAATAGAAGATGTCTGGCATCTA
    .         .         .         .         .
PheGlyThrSerIleLysProCysValLysLeuThrProLeuCys
TTCGAGACATCAATAAAACCATGTGTGAAACTAACACCTTTATGT
         .         .        300          .
ValAlaMetLysCysSerSerThrGluSerSerThrGlyAsnAsn
GTAGCAATGAAATGCAGCAGCACAGAGAGCAGCACAGGGAACAAC
    .         .         .         .         .
ThrThrSerLysSerThrSerThrThrThrThrThrProThrAsp
ACAACCTCAAAGAGCACAAGCACAACCACAACCACACCCAGAGAG
         .         .         .        400
GlnGluGlnGluIleSerGluAspThrProCysAlaArgAlaAsp
CAGGAGCAAGAGATAAGTGAGGATACTCCATGCGCACGCGCAGAC
    .         .         .         .         .
AsnCysSerGlyLeuGlyGluGluGLuThrIleAsnCysGlnPhe
AACTGCTCAGGATTGGGAGAGGAAGAAACGATCAATTGCCAGTTC
         .         .         .         .
AsnMetThrGlyLeuGluArgAspLysLysLysGlnTyrAsnGlu
AATATGACAGGATTAGAAAGAGATAAGAAAAAACAGTATAATGAA
  500          .         .         .         .
ThrTrpTyrSerLysAspValValCysGluThrAsnAsnSerThr
ACATGGTACTCAAAAGATGTGGTTTGTGAGACAAATAATAGCACA
         .         .         .         .
AsnGlnThrGlnCysTyrMetAsnHisCysAsnThrSerValIle
AATCAGACCCAGTGTTACATGAACCATTGCAACACATCAGTCATC
    .       600            .         .         .
ThrGluSerCysAspLysHisTyrTrpAspAlaIleArgPheArg
ACAGAATCATGTGACAAGCACTATTGGGATGCTATAAGGTTTAGA
         .         .         .         .
TyrCysAlaProProGlyTyrAlaLeuLeuArgCysAsnAspThr
TACTGTGCACCACCGGGTTATGCCCTATTAAGATGTAATGATACC
    .         .       700          .         .
AsnTrySerGlyPheAlaProAsnCysSerLysValValAlaSer
AATTATTCAGGCTTTGCACCCAACTGTTCTAAAGTAGTAGCTTCT
         .         .         .         .
ThrCysThrArgMetMetGluThrGlnThrSerThrTrpPheGly
ACATGCACCAGGATGATGGAAACGCAAACTTCCACATGGTTTGGC
```

-continued

```
    .         .         .       800          .
PheAsnGlyThrArgAlaGluAsnArgThrTyrIleTyrTrpHis
TTTAATGGCACTAGAGCAGAGAATAGAACATATATCTATTGGCAT
         .         .         .         .
GlyArgAspAsnArgThrIleIleSerLeuAsnLysTyrTyrAsn
GGCAGAGATAATAGAACTATCATCAGCTTAAACAAATATTATAAT
    .         .         .         .       900
LeuSerLeuHisCysLysArgProGlyAsnLysThrValLysGln
CTCAGTTTGCATTGTAAGAGGCCAGGGAATAAGACAGTGAAACAA
         .         .         .         .
IleMetLeuMetSerGlyHisValPheHisSerHisTyrGlnPro
ATAATGCTTATGTCAGGACATGTGTTTCACTCCCACTACCAGCCG
    .         .         .         .         .
IleAsnLysArgProArgGlnAlaTrpCysTrpPheLysGluLys
ATCAATAAAAGACCCAGACAAGCATGGTGCTGGTTCAAAGGCAAA
      1000         .         .         .
TrpLysAspAlaMetGlnGluValLysThrLeuAlaLysHisPro
TGGAAAGACGCCATGCAGGAGGTGAAGACCCTTGCAAAACATCCC
    .         .         .         .         .
ArgTyrArgGlyThrAsnAspThrArgAsnIleSerPheAlaAla
AGGTATAGAGGAACCAATGACACAAGGAATATTAGCTTTGCAGCG
         .       1100          .         .
ProGlyLysGlySerAspProGluValAlaTyrMetTrpThrAsn
CCAGGAAAAGGCTCAGACCCAGAAGTAGCATACATGTGGACTAAC
    .         .         .         .         .
CysArgGlyGluPheLeuTyrCysAsnMetThrTrpPheLeuAsn
TGCAGAGGAGAGTTTCTCTACTGCAACATGACTTGGTTCCTCAAT
         .         .       1200          .
TrpIleGluAsnLysThrHisArgAsnTyrAlaProCysHisIle
TGGATAGAGAATAAGACACACCGCAATTATGCACCGTGCCATATA
    .         .         .         .         .
LysGlnIleIleAsnThrTrpHisLysValGlyArgAsnValTyr
AAGCAAATAATTAACACATGGCATAAGGTAGGGAGAAATGTATAT
         .         .         .      1300
LeuProProArgGluGlyGluLeuSerCysAsnSerThrValThr
TTGCCTCCCAGGGAAGGGGAGCTGTCCTGCAACTCAACAGTAACC
    .         .         .         .         .
SerIleIleAlaAsnIleAspTrpGlnAsnAsnAsnGlnThrAsn
AGCATAATTGCTAACATTGACTGGCAAAACAATAATCAGACAAAC
         .         .         .         .
IleThrPheSerAlaGluValAlaGluLeuTyrArgLeuGluLeu
ATTACCTTTAGTGCAGAGGTGGCAGAACTATACAGATTGGAGTTG
 1400          .         .         .         .
GlyAspTyrLysLeuValGluIleThrProIleGlyPheAlaPro
GGAGATTATAAATTGGTAGAAATAACACCAATTGGCTTCGCACCT
         .         .         .         .
ThrLysGluLysArgThrSerSerAlaHisGlyArgHisThrArg
ACAAAAGAAAAAAGATACTCCTCTGCTCACGGGAGACATACAAGA
    .       1500           .         .         .
GlyValPheValLeuGlyPheLeuGlyPheLeuAlaThrAlaGly
GGTGTGTTCGTGCTAGGGTTCTTGGGTTTTCTCGCAACAGCAGGT
         .         .         .         .
SerAlaMetGlyAlaArgAlaSerLeuThrValSerAlaGlnSer
TCTGCAATGGGCGCTCGAGCGTCCCTGACCGTGTCGGCTCAGTCC
    .         .       1600           .         .
ArgThrLeuLeuAlaGlyIleValGlnGlnGlnGlnGlnLeuLeu
CGGACTTTACTGGCCGGGATAGTGCAGCAACAGCAACAGCTGTTG
         .         .         .         .
AspValValLysArgGlnGlnGluLeuLeuArgLeuThrValTrp
GACGTGGTCAAGAGACAACAAGAACTGTTGCGACTGACCGTCTGG
    .         .         .      1700          .
GlyThrLysAsnLeuGlnAlaArgValThrAlaIleGluLysTyr
GGAACGAAAAACCTCCAGGCAAGAGTCACTGCTATAGAGAAGTAG
         .         .         .         .
LeuGluAspGlnAlaArgLeuAsnSerTrpGlyCysAlaPheArg
CTACAGGACCAGGCGCGGCTAAATTCATGGGGATGTGCGTTTAGA
    .         .         .         .      1800
GlnValCysHisThrThrValProTrpValAsnAspSerLeuAla
CAAGTCTGCCACACTACTGTACCATGGGTTAATGATTCCTTAGCA
```

-continued

```
ProAspTrpAspAsnMetThrTrpGlnGluTrpGlyLysGlnVal
CCTGACTGGGACAATATGACGTGGCAGGAATCCCAAAAACAAGTC

ArgTyrLeuGluAlaAsnIleSerLysSerLeuGluGlnAlaGln
CGCTACCTGGAGGCAAATATCAGTAAAAGTTTAGAACAGGCACAA
                 1900
IleGlnGlnLeuLysAsnMetTyrGluLeuGlnLysLeuAsnSer
ATTCAGCAAGAGAAAAATATGTATGAACTACAAAAATTAAATAGC

TrpAspIlePheGlyAsnTrpPheAspLeuThrSerTrpValLys
TGGGATATTTTTGGCAATTGGTTTGACTTAACCTCCTGGGTCAAG
                 2000
TyrIleGlnTyrGlyValLeuIleIleValAlaValIleALaLeu
TATATTCAATATGGAGTGCTTATAATAGTAGCAGTAATAGCTTTA

ArgIleValIleTyrValValGlnMetLeuSerArgLeuArgLys
AGAATAGTGATATATGTAGTACAAATGTTAAGTAGGCTTAGAAAG
                 2100
GlyTyrArgProValPheSerSerProProGlyTyrIleGln***
GGCTATAGGCCTGTTTTCTCTTCCCCCCCCGGTTATATCCAATAG

IleHisIleHisLysAspArgGlyGlnProAlaAsnGluGluThr
ATCCATATCCACAAGGACCGGGGACAGCCAGCCAACGAAGAAACA
                                          2200
GluGluAspGlyGlySerAsnGlyGlyAspArgTyrTrpProTrp
CAAGAAGACGGTGGAAGCAACGGTGGAGACACATACTGGCCCTGG

ProIleAlaTyrIleHisPheLeuIleArgGlnLeuIleArgLeu
GCGATAGCATATATACATTTCCTGATCCGCCAGCTGATTCGCCTC

LeuThrArgLeuTyrSerIleCysArgAspLeuLeuSerArgSer
TTGACCAGACTATACAGCATCTGCAGGGACTTACTATCCAGGAGC
 2300
PheLeuThrLeuGlnLeuIleTyrGlnAsnLeuArgAspTrpLeu
CTCCTGACCCTCCAACTCATCTACCAGAATCTCAGAGACTGGCTG

ArgLeuArgThrAlaPheLeuGluTyrGlyCysGluTrpIleGln
AGACTTAGAACAGCCTTCTTGCAATATGGGTGCGAGTGGATCCAA
              2400
GluAlaPheGlnAlaAlaAlaAlaArgAlaThrArgGluThrLeuAla
GAAGCATTCCAGGCCGCCGCGAGGGCTACAAGAGAGACTCTTGCG

GlyAlaCysArgGlyLeuTrpArgValLeuGluArgIleGlyArg
GGCGCGTGCAGGGGCTTGTGGAGGGTATTGGAACGAATCGGGAGG
                      2500
GlyIleLeuAlaValProArgArgIleArgGlnGlyAlaGluIle
CGAATACTCGCGGTTCCAAGAAGGATCAGACAGGGAGCAGAAATC

AlaLeuLeu***GlyThrAlaValSerAlaGlyArgLeuTyrGlu
GCCCTCCTGTGAGGGACGGCAGTATCAGCAGGGAGACTTTATGAA
                            2600
TyrSerMetGluGlyProSerSerArgLysGlyGluLysPheVal
TACTCCATGGAAGGACCCAGCAGCAGAAAGGGAGAAAAATTTGTA

GlnAlaThrLysTyrGly
GAGGCAACAAAATATGGA

Gag sequence

MetGlyAlaArgAsnSerValLeuArgGlyLysLysAlaAspGlu
ATGGGCGCGAGAAACTCCGTCTTGAGAGGGAAAAAAGCAGATGAA

LeuGluArgIleArgLeuArgProGlyGlyLysLysLysTyrArg
TTAGAAAGAATCAGGTTACGGCCCGGCGGAAAGAAAAAGTACAGG

LeuLysHisIleValTrpAlaAlaAsnLysLeuAspArgPheGly
CTAAAACATATTGTGTGGGCAGCGAATAAATTGGACAGATTCGGA
       100
LeuAlaGluSerLeuLeuGluSerLysGluGlyCysGluLysIle
TTAGCAGAGAGCCTGTTGGAGTCAAAAGAGGGTTGTCAAAAAATT

LeuThrValLeuAspPrpMetValProThrGlySerGluAsnLeu
CTTACAGTTTTAGATCCAATGGTACCGACAGGTTCAGAAAATTTA
                 200
LysSerLeuPheAsnThrValCysValIleTrpCysIleHisAla
AAAAGTCTTTTTAATACTGTCTGCGTCATTTGGTGCATACACGCA

GluGluLysValLysAspThrGluGlyAlaLysGlnIleValArg
```

```
GAAGAGAAAGTGAAAGATACTGAAGGAGCAAAACAAATAGTGCGG
                      300
ArgHisLeuValAlaGluThrGlyThrAlaGluLysMetProSer
AGACATCTAGTGGCAGAAACAGGAACTGCAGAGAAAATGCCAAGG

ThrSerArgProThrAlaProSerSerGluLysGlyGlyAsnTyr
ACAAGTAGACCAACAGCACCATCTAGCGAGAAGGGAGGAAATTAC
                                          400
ProValGlnHisValGlyGlyAsnTyrThrHisIleProLeuSer
CCAGTGCAACATGTAGGCGGCAACTACACCCATATACCGCTGAGT

ProArgThrLeuAsnAlaTrpValLysLeuValGluGluLysLys
CCCCGAACCCTAAATGCCTGGGTAAAATTAGTAGAGGAAAAAAAG

PheGlyAlaGluValValProGlyPheGluAlaLeuSerGluGly
TTCGGGGCAGAAGTAGTGCCAGGATTTCAGGCACTCTCAGAAGGC
    500
CysThrProTyrAspIleAsnGlnMetLeuAsnCysValGlyAsp
TGGACGCCCTATGATATCAACCAAATGCTTAATTGTGTGGGCGAC

HisGlnAlaAlaMetGlnIleIleArgGluIleIleAsnGluGlu
CATCAAGCAGCCATGCAGATAATCAGGGAGATTATCAATGAGGAA
         600
AlaAlaGluTrpAspValGlnHisProIleProGlyProLeuPro
GCAGCAGAATGGGATGTGCAACATCCAATACCAGCCCCCTTAGCA

AlaGlyGlnLeuArgGluProArgGlySerAspIleAlaGlyThr
GCGGGGCAGCTTAGAGAGCCAAGGGGATCTGACATAGCAGGGACA
              700
ThrSerThrValGluGluGlnIleGlnTrpMetPheArgProGln
ACAAGCACAGTAGAAGAACAGATCCAGTGGATGTTTAGGCCACAA

AsnProValProValGlyAsnIleTyrArgArgTrpIleGlnIle
AATCCTGTACCAGTAGGAAACATCTATAGAAGATGGATCCAGATA
                       800
GlyLeuGlnLysCysValArgMetTyrAsnProThrAsnIleLeu
GGATTGCAGAAGTGTGTCAGGATGTACAACCCGACCAACATCCTA

AspIleLysGlnGlyProLysGluProPheGlnSerTyrValAsp
GACATAAAACAGGGACCAAAGGAGCCGTTCCAAAGCTATGTAGAT
                                          900
ArgPheTyrLysSerLeuArgAlaGluGlnThrAspProAlaVal
AGATTCTACAAAAGCTTGAGGGCAGAACAAACAGATCCAGCAGTG

LysAsnTrpMetThrGlnThrLeuLeuValGlnAsnAlaAsnPro
AAGAATTGGATGACCCAAACACTGCTAGTACAAAATGCCAACCCA

AspCysLysLeuValLeuLysGluLeuGlyMetAsnProThrLeu
GACTGTAAATTAGTGCTAAAAGGACTAGGGATGAACCCTACCTTA
                    1000
GluGluMetLeuThrAlaCysGlnGlyValGlyGlyProGlyGln
GAAGAGATGCTGACCGCCTGTCAGGGGGTAGGTGGGCCAGGCCAG

LysAlaArgLeuMetAlaGluAlaLeuLysGluValIleGlyPro
AAAGCTAGATTAATGGCAGAGGCCCTGAAAGAGGTCATAGGACCT

AlaProIleProPheAlaAlaAlaGlnGlnArgLysAlaPheLys
GCCCCTATCCCATTCGCAGCAGCCCAGCAGAGAAAGGCATTTAAA

CysTrpAsnCysGlyLysGluGlyHisSerAlaArgGlnCysArg
TGCTGGAACTGTGGAAAGGAAGGGCACTCGGCAAGACAATGCCGA
                            1200
AlaProArgArgGlnGlyCysTrpLysCysGlyLysProGlyHis
GCACCTAGAAGGCAGGGCTGCTGGAAGTGTGGTAAGCCAGGACAC

IleMetThrAsnCysProAspArgGlnAlaGlyPheLeuGlyLeu
ATCATGACAAACTGCCCCAGATAGACAGGCAGGTTTTTTAGGACTG
                                  1300
GlyProTrpGlyLysLysProArgAsnPheProValAlaGlnVal
GGCCCTTGGGGAAAGAAGCCCCGCAACTTCCCCGTGGCCCAAGTT

ProGlnGlyLeuThrProThrAlaProProValAspProAlaVal
CCGCAGGGGCTGACACCAACAGCACCCCCAGTGGATCCAGCAGTG

AspLeuLeuGluLysTyrMetGlnGlnGlyLysArgGlnArgGlu
GATCTACTGGAGAAATATATGCAGCAAGGGAAAAGACAGAGAGAG
 1400
GlnArgGluArgProTyrLysGluValThrGluAspLeuLeuHis
CAGAGAGAGAGACCATACAAGGAAGTGACAGAGGACTTACTGCAC
```

-continued

```
LeuGluGlnGlyGluThrProTyrArgGlnProProThrGluAsp
CTCGAGCAGGGGGAGACACCATACAGGGAGCCACCAACAGAGGAC
    .       1500        .         .         .
LeuLeuHisLeuAsnSerLeuPheGlyLysAspGln
TTGCTGCACCTCAATTCTCTCTTTGGAAAAGACCAG
         .      .         .
```

Example 6: Peptide Sequences Encoded By The ENV and GAG genes

The following coding regions for antigenic peptides, identified for convenience only by the nucleotide numbers of Example 5, within the env and gag gene regions are of particular interest.

```
env1 (1732–1809)
                     ArgValThrAlaIleGluLysTyr
                     AGAGTCACTGCTATAGAGAAGTAC
                             .         .
LeuGlnAspGlnAlaArgLeuAsnSerTrpGlyCysAlaPheArg
CTACAGGACCAGGCGCGGCTAAATTCATGGGGATGTGCGTTTAGA
    .         .         .         .      1800
GlnValCys
CAAGTCTGC env2 (1912–1983)
                     SerLysSerLeuGluGlnAlaGln
                     AGTAAAAGTTTAGAACAGGCACAA
                             .         .
IleGlnGlnGluLysAsnMetTyrGluLeuGlnLysLeuAsnSer
ATTCAGCAAGAGAAAAATATGTATGAACTACAAAAATTAAATAGC
1940           .         .         .         .
Trp
TGG env3 (1482–1530)
Pro ThrLysGluLysArgTyrSerSerAlaHisGlyArgHisThrArg
CCT ACAAAAGAAAAAAGATACTCCTCTGCTCACGGGAGACATACAAGA
         .      1500         .         .         .

env4 (55–129)
         CysThrGlnTyrValThrValPheTyrGlyValPro
         TGCACCCAATATGTAACTGTTTTCTATGGCGTACCC
                  .         .         .         .
ThrTrpLysAsnAlaThrIleProLeuPheCysAlaThr
ACGTGGAAAAATGCAACCATTCCCCTGTTTTGTGCAACC
       100          .         .

env5 (175–231)
                                       AspAsp
                                       GATGAT
                                            .
 TyrGlnGlnIleThrLeuAsnValThrGluAlaPheAspAlaTrp
 TATCAGGAAATAACTTTGAATGTAACAGAGGCTTTTGATGCATGG
          .       200          .         .
 AsnAsn
 AATAAT env6 (274–330)
    GluThrSerIleLysProCysValLysLeuThrProLeuCys
    GAGACATCAATAAAACCATGTGTGAAACTAACACCTTTATGT
        .          .       300          .
 ValAlaMetLysCys
 GTAGCAATGAAATGC
     .        .

env7 (607–660)
                     AsnHisCysAsnThrSerValIle
                     AACCATTGCAACACATCAGTCATC
                      610          .         .
 ThrGluSerCysAspLysHisTyrTrpAsp
 ACAGAATCATGTGACAAGCACTATTGGGAT
         .          .         .

env8 (661–720)
                             AlaIleArgPheArg
```

-continued

```
                             GCTATAAGGTTTAGA
                                           .
 TyrCysAlaProProGlyTyrAlaLeuLeuArgCysAsnAspThr
 TACTGTGCACCACCGGGTTATGCCCTATTAAGATGTAATGATACC
     .         .       700          .         .

env9 (997–1044)
       LysArgProArgGlnAlaTrpCysTrpPheLysGlyLys
       AAAAGACCCAGACAAGCATGGTGCTGGTTCAAAGGCAAA
       1000          .         .         .
 TrpLysAsp
 TGGAAAGAC env10 (1132–1215)
     LysGlySerAspProGluValAlaTyrMetTrpThrAsn
     AAAGGCTCAGACCCAGAAGTAGCATACATGTGGACTAAC
             .         .         .         .
CysArgGlyGluPheLeuTyrCysAsnMetThrTrpPheLeuAsn
TGCAGAGGAGAGTTTCTCTACTGCAACATGACTTGGTTCCTCAAT
         .         .       1200          .

env11 (1237–1305)
                     ArgAsnTyrAlaProCysHisLys
                     CGCAATTATGCACCGTGCCATATA
                             .         .     .
LysGlnIleIleAsnThrTrpHisLysValGlyArgAsnValTyr
AAGCAAATAATTAACACATGGCATAAGGTAGGGAGAAATGTATAT
         .         .         .       1300 gag1 (991–1053)
AspCysLysLeuValLeuLysGlyLeuGlyMetAsnProThrLeu
GACTGTAAATTAGTGCTAAAAGGACTAGGGATGAACCCTACCTTA
      1000           .         .         .
GluGluMetLeuThrAla
GAAGAGATGCTGACCGCC
    .         .
```

Of the foregoing peptides, env1, and env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the HIV group. For vaccinating purposes, the fore going peptides may be coupled to a carrier protein by utilizing. suitable and well known techniques to enhance the host's immune response. Adjuvants such as calcium phosphate or alum hydroxide may also be added. The foregoing peptides can be synthesized by conventional protein synthesis techniques, such as that of Merrifield.

It will pre apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| DNA CODON | | | | | AMINO ACID 3 LET. | | | | AMINO ACID 1 LET. | | | | |
|---|---|---|---|---|---|---|---|---|---|---|---|---|---|
| | \2: | T | C | A | G | T | C | A | G | T | C | A | G |
| 1 | 3\: | | | | | | | | | | | | |
| | T: | TTT | TCT | TAT | TGT | PHE | SER | TYR | CYS | F | S | Y | C |
| T | C: | TTC | TCC | TAC | TGC | PHE | SER | TYR | CYS | F | S | Y | C |
| | A: | TTA | TCA | TAA | TGA | LEU | SER | *** | *** | L | S | * | * |
| | G: | TTG | TCG | TAG | TGG | LEU | SER | *** | TRP | L | S | * | W |
| | T: | CTT | CCT | CAT | CGT | LEU | PRO | HIS | ARG | L | P | H | R |
| C | C: | CTC | CCC | CAC | CGC | LEU | PRO | HIS | ARG | L | P | H | R |
| | A: | CTA | CCA | CAA | CGA | LEU | PRO | GLN | ARG | L | P | Q | R |
| | G: | CTG | CCG | CAG | CGG | LEU | PRO | GLN | ARG | L | P | Q | R |
| | T: | ATT | ACT | AAT | AGT | ILE | THR | ASN | SER | I | T | N | S |
| A | C: | ATC | ACC | AAC | AGC | ILE | THR | ASN | SER | I | T | N | S |
| | A: | ATA | ACA | AAA | AGA | ILE | THR | LYS | ARG | I | T | K | R |
| | G: | ATG | ACG | AAG | AGG | MET | THR | LYS | ARG | M | T | K | R |
| | T: | GTT | GCT | GAT | GGT | VAL | ALA | ASP | GLY | V | A | D | G |
| G | C: | GTC | GCC | GAC | GGC | VAL | ALA | ASP | GLY | V | A | D | G |
| | A: | GTA | GCA | GAA | GGA | VAL | ALA | GLU | GLY | V | A | E | G |
| | G: | GTG | GCG | GAG | GGG | VAL | ALA | GLU | GLY | V | A | E | G |

| 3 Letter | 1 Letter | CODONS | | | | | |
|---|---|---|---|---|---|---|---|
| ALA | A | GCT | GCC | GCA | GCG | | |
| ARG | R | CGT | CGC | CGA | CGG | AGA | AGG |
| ASN | N | AAT | AAC | | | | |
| ASP | D | GAT | GAC | | | | |
| CYS | C | TGT | TCC | | | | |
| GLN | Q | CAA | CAG | | | | |
| GLU | E | GAA | GAG | | | | |
| GLY | G | GGT | GGC | GGA | GGG | | |
| HIS | H | CAT | CAC | | | | |
| ILE | I | ATT | ATC | ATA | | | |
| LEU | L | CTT | CTC | CTA | CTG | TTA | TTG |
| LYS | K | AAA | AAG | | | | |
| MET | M | ATG | | | | | |
| PHE | F | TTT | TTC | | | | |
| PRO | P | CCT | CCC | CCA | CCG | | |
| SER | S | TCT | TCC | TCA | TCG | AGT | AGC |
| THR | T | ACT | ACC | ACA | ACG | | |
| TRP | W | TGG | | | | | |
| TYR | Y | TAT | TAC | | | | |
| VAL | V | GTT | GTC | GTA | GTG | | |
| *** | * | TAA | TAG | TGA | | | |

What is claimed is:

1. A cloned nucleic acid of a human immunodeficiency virus type 2 (HIV-2), wherein the nucleic acid is isolated from other human immunodeficiency viral nucleic acids, having the following sequences:

```
        10         20         30         40
GGTCGCTCTG CGGAGAGGCT GGCAGATTGA GCCCTGGGAG 50         60         70         80
GTTCTCTCCA GCACTAGCAG GTAGAGCCTG GGTGTTCCCT 90        100        110        120
GCTAGACTCT CACCAGCACT TGGCCGGTGC TGGGCAGACG 130        140        150        160
GCCCCACGCT TGCTTGCTTA AAAACCTCTT AATAAAGCTG 170        180        190        200
CCAGTTAGAA GCAAGTTAAG TGTGTGCTCC CATCTCTCCT 210        220        230        240
AGTCGCCGCC TGGTCATTCG GTGTTCACCT GAGTAACAAG 250        260        270        280
ACCCTGGTCT GTTAGGACCC TTCTTGCTTT GGGAAACCGA 290        300        310        320
GGCAGGAAAA TCCCTAGCAG GTTGGCGCCT GACAGGGAC
```

-continued

```
       330        340        350        360
TTGAAGAAGA CTGAGAAGTC TTGGAACACG GCTGAGTGAA 370        380        390        400
GGCAGTAAGG GCGGCAGGAA CAAACCACGA CGGAGTGCTC 410        420        430        440
CTAGAAAGGC GCGGGCCGAG GTACCAAAGG CAGCGTGTGG 450        460        470        480
AGCGGGAGGA GAAGAGGCCT CCGGGTGAAG GTAAGTACCT 490        500        510        520
ACACCAAAAA CTGTAGCCGA AAGGGCTTGT TATCCTACCT 530        540        550        560
TTAGACAGGT AGAAGATTGT GGGAGATGGG CGCGAGAAAC 570        580        590        600
TCCGTCTTGA GAGGGAAAAA AGCAGATGAA TTAGAAAGAA 610        620        630        640
TCAGGTTACG GCCCGGCGGA AAGAAAAAGT ACAGGCTAAA 650        660        670        680
ACATATTGTG TGGGCAGCGA ATAAATTGGA CAGATTCGGA 690        700        710        720
TTAGCAGAGA GCCTGTTGGA CTCAAAAGAG GGTTGTCAAA
```

```
      730        740        750        760
AAATTCTTAC AGTTTTAGAT CCAATGGTAC CGACAGGTTC 770        780        790        800
AGAAAATTTA AAAAGTCTTT TTAATACTGT CTGCGTCATT 810        820        830        840
TGGTGCATAC ACGCAGAAGA GAAAGTGAAA GATACTGAAG 850        860        870        880
GAGCAAAACA AATAGTGCGG AGACATCTAG TGGCAGAAAC 890        900        910        920
AGGAACTGCA GAGAAAATGC CAAGCACAAG TAGACCAACA 930        940        950        960
GCACCATCTA GCGAGAAGGG AGGAAATTAC CCAGTGCAAC 970        980        990       1000
ATGTAGGCGG CAACTACACC CATATACCGC TGAGTCCCCG 1010       1020       1030       1040
AACCCATAAT GCCTGGGTAA AATTAGTAGA GGAAAAAAAG 1050       1060       1070       1080
TTCGGGGCAG AAGTAGTGCC AGGATTTCAG GCACTCTCAG 1090       1100       1110       1120
AAGGCTGCAC GCCCTATGAT ATCAACCAAA TGCTTAATTG 1130       1140       1150       1160
TGTGGGCGAC CATCAAGCAG CCATGCAGAT AATCAGGGAG 1170       1180       1190       1200
ATTATCAATG AGGAAGCAGC AGAATGGGAT GTGCAACATC 1210       1220       1230       1240
CAATACCAGG CCCCTTACCA GCGGGGCAGC TTAGAGAGCC 1250       1260       1270       1280
AAGGGGATCT GACATAGCAG GGACAACAAG CACAGTAGAA 1290       1300       1310       1320
GAACAGATCC AGTGGATGTT TAGGCCACAA AATCCTGTAC 1330       1340       1350       1360
CAGTAGGAAA CATCTATAGA AGATGGATCC AGATAGGATT 1370       1380       1390       1400
GCAGAAGTGT GTCAGGATGT ACAACCCGAC CAACATCCTA 1410       1420       1430       1440
GACATAAAAC AGGGACCAAA GGAGCCGTTC CAAAGCTATG 1450       1460       1470       1480
TAGATAGATT CTACAAAAGC TTGAGGGCAG AACAAACAGA 1490       1500       1510       1520
TCCAGCAGTG AAGAATTGGA TGACCCAAAC ACTGCTAGTA 1530       1540       1550       1560
CAAAATGCCA ACCCAGACTG TAAATTAGTG CTAAAAGGAC 1570       1580       1590       1600
TAGGGATGAA CCCTACCTTA GAAGAGATGC TGACCGCCTG 1610       1620       1630       1640
TCAGGGGGTA GGTGGGCCAG GCCAGAAAGC TAGATTAATG 1650       1660       1670       1680
GCAGAGGCCC TGAAAGAGGT CATAGGACCT GCCCCTATCC 1690       1700       1710       1720
CATTCGCAGC AGCCCAGCAG AGAAAGGCAT TTAAATGCTG 1730       1740       1750       1760
GAACTGTGGA AAGGAAGGGC ACTCGGCAAG ACAATGCCGA 1770       1780       1790       1800
GCACCTAGAA GGCAGGGCTG CTGGAAGTGT GGTAAGCCAG
```

```
     1810       1820       1830       1840
GACACATCAT GACAAAGTGC CCAGATAGAC AGGCAGGTTT 1850       1860       1870       1880
TTTAGGACTG GGCCCTTGGG GAAAGAAGCC CCGCAACTTC 1890       1900       1910       1920
CCCGTGGCCC AAGTTCCGCA GGGGCTGACA CCAACAGCAC 1930       1940       1950       1960
CCCCAGTGGA TCCAGCAGTG GATCTACTGG AGAAATATAT 1970       1980       1990       2000
GCAGCAAGGG AAAAGACAGA GAGAGCAGAG AGAGAGACCA 2010       2020       2030       2040
TACAAGGAAG TGACAGAGGA CTTACTGCAC CTCGAGCAGG 2050       2060       2070       2080
GGGAGACACC ATACAGGGAG CCACCAACAG AGGACTTGCT 2090       2100       2110       2120
GCACCTCAAT TCTCTCTTTG GAAAAGACCA GTAGTCACAG 2130       2140       2150       2160
CATACATTGA GGGTCAGCCA GTAGAAGTCT TGTTAGACAC 2170       2180       2190       2200
AGGGGCTGAC GACTCAATAG TAGCAGGAAT AGAGTTAGGG 2210       2220       2230       2240
AACAATTATA GCCCAAAAAT AGTAGGGGGA ATAGGGGGAT 2250       2260       2270       2280
TCATAAATAC CAAGGAATAT AAAAATGTAG AAATAGAAGT 2290       2300       2310       2320
TCTAAATAAA AAGGTACGGG CCACCATAAT GACAGGCGAC 2330       2340       2350       2360
ACCCCAATCA ACATTTTTGG CAGAAATATT CTGACAGCCT 2370       2380       2390       2400
TAGGCATGTC ATTAAATCTA CCAGTCGCCA AAGTAGAGCC 2410       2420       2430       2440
AATAAAAATA ATGCTAAAGC CAGGGAAAGA TGGACCAAAA 2450       2460       2470       2480
CTGAGACAAT GGCCCTTAAC AAAAGAAAAA ATAGAAGCAC 2490       2500       2510       2520
TAAAAGAAAT CTGTGAAAAA ATGGAAAAAG AAGGCCAGCT 2530       2540       2550       2560
AGAGGAAGCA CCTCCAACTA ATCCTTATAA TACCCCCACA 2570       2580       2590       2600
TTTGCAATCA AGAAAAAGGA CAAAAACAAA TGGAGGATGC 2610       2620       2630       2640
TAATAGATTT CAGAGAACTA AACAAGGTAA CTCAAGATTT 2650       2660       2670       2680
CACAGAAATT CAGTTAGGAA TTCCACACCC AGCAGGGTTG 2690       2700       2710       2720
GCCAAGAAGA GAAGAATTAC TGTACTAGAT GTAGGGGATG 2730       2740       2750       2760
CTTACTTTTC CATACCACTA CATGAGGACT TTAGACCATA 2770       2780       2790       2800
TACTGCATTT ACTCTACCAT CAGTGAACAA TGCAGAACCA 2810       2820       2830       2840
GGAAAAAGAT ACATATATAA AGTCTTGCCA CAGGGATGGA 2850       2860       2870       2880
```

-continued

```
              AGGGATCACC AGCAATTTTT CAACACACAA TGAGACAGGT 2890       2900       2910       2920
              ATTAGAACCA TTCAGAAAAG CAAACAAGGA TGTCATTATC 2930       2940       2950       2960
              ATTCAGTACA TGGATGATAT CTTAATAGCT AGTGACAGGA 2970       2980       2990       3000
              CAGATTTAGA ACATGATAGG GTAGTCCTGC AGCTCAAGGA 3010       3020       3030       3040
              ACTTCTAAAT GGCCTAGGAT TTTCTACCCC AGATGAGAAG 3050       3060       3070       3080
              TTCCAAAAAG ACCCTCCATA CCACTGGATG GGCTATGAAC 3090       3100       3110       3120
              TATGGCCAAC TAAATGGAAG TTGCAGAAAA TACAGTTGCC 3130       3140       3150       3160
              CCAAAAAGAA ATATGGACAG TCAATGACAT CCAGAAGCTA 3170       3180       3190       3200
              GTGGGTGTCC TAAATTGGGC AGCACAACTC TACCCAGGGA 3210       3220       3230       3240
              TAAAGACCAA ACACTTATGT AGGTTAATCA GAGGAAAAAT 3250       3260       3270       3280
              GACACTCACA GAAGAAGTAC AGTGGACAGA ATTAGCAGAA 3290       3300       3310       3320
              GCAGAGCTAG AAGAAAACAG AATTATCCTA AHCCAHHAAC 3330       3340       3350       3360
              AAGAGGGACA CTATTACCAA GAAGAAAAAG AGCTAGAAGC 3370       3380       3390       3400
              AACAGTCCAA AAGGATCAAG AGAATCAGTG GACATATAAA 3410       3420       3430       3440
              ATACACCAGG AAGAAAAAAT TCTAAAAGTA GGAAAATATG 3450       3460       3470       3480
              CAAAGGTGAA AAAGACCCAT ACCAATGGAA TCAGATTGTT 3490       3500       3510       3520
              AGCACAGGTA GTTCAGAAAA TAGGAAAAGA AGCACTAGTC 3530       3540       3550       3560
              ATTTGGGGAC GAATACCAAA ATTTCACCTA CCAGTAGAGA 3570       3580       3590       3600
              GAGAAATCTC GGAGCAGTGG TGGGATAACT ACTGGCAAGT 3610       3620       3630       3640
              GACATGGATC CCAGACTGGG ACTTCGTGTC TACCCCACCA 3650       3660       3670       3680
              CTGGTCAGGT TAGCGTTTAA CCTGGTAGGG GATCCTATAC 3690       3700       3710       3720
              CAGGTGCAGA GACCTTCTAC ACAGATGGAT CCTGCAATAG 3730       3740       3750       3760
              GCAATCAAAA GAAGGAAAAG CAGGATATGT AACAGATAGA 3770       3780       3790       3800
              GGGAAAGACA AGGTAAAGAA ACTAGAGCAA ACTACCAATC 3810       3820       3830       3840
              AGCAAGCAGA ACTAGAAGCC TTTGCGATGG CACTAACAGA 3850       3860       3870       3880
              CTCGGGTCCA AAAGTTAATA TTATAGTAGA CTCACAGTAT 3890       3900       3910       3920
              GTAATGGGGA TCAGTGCAAG CCAACCAACA GAGTCAGAAA
```

```
              3930       3940       3950       3960
              GTAAAATAGT GAACCAGATC ATAGAAGAAA TGATAAAAAA 3970       3980       3990       4000
              GGAAGCAATC TATGTTGCAT GGGTCCCAGC CCACAAAGGC 4010       4020       4030       4040
              ATAGGGGAA ACCAGGAAGT AGATCATTTA GTGAGTCAGG 4050       4060       4070       4080
              GTATCAGACA AGTGTTGTTC CTGGAAAAAA TAGAGCCCGC 4090       4100       4110       4120
              TCAGGAAGAA CATGAAAAAT ATCATAGCAA TGTAAAAGAA 4130       4140       4150       4160
              CTGTCTCATA AATTTGGAAT ACCCAATTTA GTGGCAAGGC 4170       4180       4190       4200
              AAATAGTAAA CTCATGTGCC CAATGTCAAC AGAAAGGGGA 4210       4220       4230       4240
              AGCTATACAT GGGCAAGTAA ATGCAGAACT AGGCACTTGG 4250       4260       4270       4280
              CAAATGGACT GCACACATTT AGAAGGAAAG ATCATTATAG 4290       4300       4310       4320
              TAGCAGTACA TGTTGCAAGT GGATTTATAG AAGCAGAAGT 4330       4340       4350       4360
              CATCCCACAG GAATCAGGAA GACAAACAGC ACTCTTCCTA 4370       4380       4390       4400
              TTGAAACTGG CAAGTAGGTG GCCAATAACA CACTTGCATA 4410       4420       4430       4440
              CAGATAATGG TGCCAACTTC ACTTCACAGG AGGTGAAGAT 4450       4460       4470       4480
              GGTAGCATGG TGGATAGGTA TAGAACAATC CTTTGGAGTA 4490       4500       4510       4520
              CCTTACAATC CACAGAGCCA AGGAGTAGTA GAAGCAATGA 4530       4540       4550       4560
              ATCACCATCT AAAAAACCAA ATAAGTAGAA TCAGAGAACA 4570       4580       4590       4600
              GGCAAATACA ATAGAAACAA TAGTACTAAT GGCAATTCAT 4610       4620       4630       4640
              TGCATGAATT TTAAAAGAAG GGGGGAATA GGGGATATGA 4650       4660       4670       4680
              CTCCATCAGA AAGATTAATC AATATGATCA CCACAGAACA 4690       4700       4710       4720
              AGAGATACAA TTCCTCCAAG CCAAAAATTC AAAATTAAAA 4730       4740       4750       4760
              GATTTTCGGG TCTATTTCAG AGAAGGCAGA GATCAGTTGT 4770       4780       4790       4800
              GGAAAGGACC TGGGAACTA CTGTGGAAAG GAGAAGGAGC 4810       4820       4830       4840
              AGTCCTAGTC AAGGTAGGAA CAGACATAAA AATAATACCA 4850       4860       4870       4880
              AGAAGGAAAG CCAAGATCAT CAGAGACTAT GGAGGAAGAC 4890       4900       4910       4920
              AAGAGATGGA TAGTGGTTCC CACCYHHAHH GTGCCAGGGA 4930       4940       4950       4960
              GGATGGAGAA ATGGCATAGC CTTGTCAAGT ATCTAAAATA 4970       4980       4980       5000
              CAAAACAAAG GATCTAGAAA AGGTGTGCTA TGTTCCCCAC
```

-continued

```
        5010       5020       5030       5040
   CATAAGGTGG GATGGGCATG GTGGACTTGT AGCAGGGTAA 5050       5060       5070       5080
   TATTCCCATT AAAAGGAAAC AGTCATCTAG AGATACAGGC 5090       5100       5110       5120
   ATATTGGAAC TTAACACCAG AAAAAGGATG GCTCTCCTCT 5130       5140       5150       5160
   TATTCAGTAA GAATAACTTG GTACACAGAA AAGTTCTGGA 5170       5180       5190       5200
   CAGATGTTAC CCCAGACTGT GCAGATGTCC TAATACATAG 5210       5220       5230       5240
   CACTTATTTC CCTTGCTTTA CAGCAGGTGA AGTAAGAAGA 5250       5260       5270       5280
   GCCATCAGAG GGGAAAAGTT ATTGTCCTGC TGCAATTATC 5290       5300       5310       5320
   CCCGAGCTCA TAGAGCCCAG GTACCGTCAC TTCAATTTCT 5330       5340       5350       5360
   GGCCTTAGTG GTAGTGCAAC AAAATGACAG ACCCCAGAGA 5370       5380       5390       5400
   GACAGTACCA CCAGGAAAGA GCGGCGAAGA GACTATCGGA 5410       5420       5430       5440
   GAGGCCTTCG CCTGGCTAAA CAGGACAGTA GAAGCCATAA 5450       5460       5470       5480
   ACAGAGAACG AGTGAATCAC CTACCCCGAG AACTTATTTT 5490       5500       5510       5520
   CCAGGTGTGG CAGAGGTCCT GGAGATACTG GCATGATGAA 5530       5540       5550       5560
   CAAGGGATGT CAGAAAGTTA CACAAAGTAT AGATATTTGT 5570       5580       5590       5600
   GCATAATACA GAAAGCAGTG TACATGCATG TTACCAAAGG 5610       5620       5630       5640
   GTGTACTTGC GTGGGAGGG GACATGGGCC AGGAGGGTCG 5650       5660       5670       5680
   AGACCAGGGC CTCCTCCTCC TCCCCCTCCA GGTCTGGTCT 5690       5700       5710       5720
   AATGGCTGAA GCACCAACAG AGCTCCCCCC GGTGAATGGG 5730       5740       5750       5760
   ACCCCACTGA GGGAGCCAGG GGATGAGTGG ATAATAGAAA 5770       5780       5790       5800
   TCTTGAGAGA AATAAAAGAA GAAGCTTTAA AGCATTTTGA 5810       5820       5830       5840
   CCCTCGCTTG CTAATTGCTC TTGGCAAATA TATCTATACT 5850       5860       5870       5880
   AGACATGGAG ACACCCTTGA AGGCGCCAGA GAGCTCATTA 5890       5900       5910       5920
   AAGTCCTGCA ACGAGCCCTT TTCACGCACT TCAGAGCAGG 5930       5940       5950       5960
   ATGTGGCCAC TCAAGAATTG GCCAGACAAG GGGAGGAAAT 5970       5980       5990       6000
   CCTCTCTCAG CTATACCGAC CCCTAGAAAC ATGCAATAAC 6010       6020       6030       6040
   TCATGCTATT GTAAGCGATG CTCGTACCAT TGTCAGATGT 6050       6060       6070       6080
```

-continued

```
   GTTTTCTAAA CAAGGGGCTC GGGATATGTT ATGAACGAAA 6090       6100       6110       6120
   GGGCAGACGA AGAAGGACTC CAAAGAAAAC TAAGACTCAT 6130       6140       6150       6160
   CCGTCTCCTA CACCAGACAA GTGAGTATGA TGAATCAGCT 6170       6180       6190       6200
   GCTTATTGCC ATTTTATTAG CTAGTGCTTG CTTAGTATAT 6210       6220       6230       6240
   TGCACCCAAT ATGTAACTGT TTTCTATGGC GTACCCACGT 6250       6260       6270       6280
   GGAAAAATGC AACCATTCCC CTCTTTTGTG CAACCAGAAA 6290       6300       6310       6320
   TAGGGATACT TGGGGAACCA TACAGTGCTT GCCTGACAAT 6330       6340       6350       6360
   GATGATTATC AGGAAATAAC TTTGAATGTA ACAGAGGCTT 6370       6380       6390       6400
   TTGATGCATG GAATAATACA GTAACAGAAC AAGCAATAGA 6410       6420       6430       6440
   AGATGTCTGG CATCTATTCG AHACAYCAAY AAAACCATGT 6450       6460       6470       6480
   GTCAAACTAA CACCTTTATG TGTAGCAATG AAATGCAGCA 6490       6500       6510       6520
   GCACAGAGAG CAGCACAGGG AACAACACAA CCTCAAAGAG 6530       6540       6550       6560
   CACAAGCACA ACCACAACCA CACCCACAGA CCAGGAGCAA 6570       6580       6590       6600
   GAGATAAGTG AGGATACTCC ATGCGCACGC GCAGACAACT 6610       6620       6630       6640
   GCTCAGGATT GGGAGAGGAA GAAACGATCA ATTGCCAGTT 6650       6660       6670       6680
   CAATATGACA GGATTAGAAA GAGATAAGAA AAAAGAGTAT 6690       6700       6710       6720
   AATGAAACAT GGTACTCAAA AGATGTGGTT TGTGAGACAA 6730       6740       6750       6760
   ATAATAGCAC AAATCAGACC CAGTGTTACA TGAACCATTG 6770       6780       6790       6800
   CAACACATCA GTCATCACAG AATCATGTGA CAAGCACTAT 6810       6820       6830       6840
   TGGGATGCTA TAAGGTTTAG ATACTGTGCA CCACCGGGTT 6850       6860       6870       6880
   ATGCCCTATT AAGATGTAAT GATACCAATT ATTCAGGCTT 6890       6900       6910       6920
   TGCACCCAAC TGTTCTAAAG TAGTAGCTTC TACATGCACC 6930       6940       6950       6960
   AGGATGATGG AAACHCAAAC TTCCACATGG TTTGGCTTTA 6970       6980       6990       7000
   ATGGCACTAG AGCAGAGAAT AGAACATATA TCTATTGGCA 7010       7020       7030       7040
   TGGCAGAGAT AATAGAACTA TCATCAGCCT AAACAAATAT 7050       7060       7070       7080
   TATAATCTCA GTTTGCATTG TAAGAGGCCA GGGAATAAGA 7090       7100       7110       7120
   CAGTGAAACA AATAATGCTT ATGTCAGGAC ATGTGTTTCA
```

-continued

```
        7130       7140       7150       7160
    CTCCCACTAC CAGCCGATCA ATAAAAGACC CAGACAAGCA 7170       7180       7190       7200
    TGGTGCTGGT TCAAAGGCAA ATGGAAAGAC GCCATGCAGG 7210       7220       7230       7240
    AGGTGAAGGA AACCCTTGCA AAACATCCCA GGTATAGAGG 7250       7260       7270       7280
    AACCAATGAC ACAAGGAATA TTAGCTTTGC AGCGCCAGGA 7290       7300       7310       7320
    AAAGGCTCAG ACCCAGAAGT AGCATACATG TGGACTAACT 7330       7340       7350       7360
    GCAGAGGAGA GTTTCTCTAC TGCAACATGA CTTGGTTCCT 7370       7380       7390       7400
    CAATTGGATA GAGAATAAGA CACACCGCAA TTATGCACCG 7410       7420       7430       7440
    TGCCATATAA AGCAAATAAT TAACACATGG CATAAGGTAG 7450       7460       7470       7480
    GGAGAAATGT ATATTTGCCT CCCAGGGAAG GGGAGCTGTC 7490       7500       7510       7520
    CTGCAACTCA ACAGTAACCA GCATAATTGC TAACATTGAC 7530       7540       7550       7560
    TGGCAAAACA ATAATCAGAC AAACATTACC TTTAGTGCAG 7570       7580       7590       7600
    AGGTGGCAGA ACTATACAGA TTGGAGTTGG GAGATTATAA 7610       7620       7630       7640
    ATTGGTAGAA ATAACACCAA TTGGCTTCGC ACCTACAAAA 7650       7660       7670       7680
    GAAAAAAGAT ACTCCTCTGC TCACGGGAGA CATACAAGAG 7690       7700       7710       7720
    GTGTGTTCGT GCTAGGGTTC TTGGGTTTTC TCGCAACAGC 7770       7780       7790       7800
    CAGTCCCGGA CTTTACTGGC CGGGATAGTG CAGCAACAGC 7810       7820       7830       7840
    AACAGCTGTT GGACGTGGTC AAGAGACAAC AAGAACTGTT 7850       7860       7870       7880
    GCGACTGACC GTCTGGGGAA CGAAAAACCT CCAGGCAAGA 7890       7900       7910       7920
    GTCACTGCTA TAGAGAAGTA CCTACAGGAC CAGGCGCGGC 7930       7940       7950       7960
    TAAATTCATG GGGATGTGCG TTTAGACAAG TCTGCCACAC 7970       7980       7990       8000
    TACTGTACCA TGGGTTAATG ATTCCTTAGC ACCTGACTGG 8010       8020       8030       8040
    GACAATATGA CGTGGCAGGA ATGGGAAAAA CAAGTCCGCT 8050       8060       8070       8080
    ACCTGGAGGC AAATATCAGT AAAAGTTTAG AACAGGCACA 8090       8100       8110       8120
    AATTCAGCAA GAGAAAAATA TGTATGAACT ACAAAAATTA 8130       8140       8150       8160
    ATATTTTTGG ATATTTTTGG CAATTGGTTT GACTTAACCT 8170       8180       8190       8200
    CCTGGGTCAA GTATATTCAA TATGGAGTGC TTATAATAGT 8210       8220       8230       8240
    AGCAGTAATA GCTTTAAGAA TAGTGATATA TGTAGTACAA
```

```
        8250       8260       8270       8280
    ATGTTAAGTA GGCTTAGAAA GGGCTATAGG CCTGTTTTCT 8290       8300       8310       8320
    CTTCCCCCCC CGGTTATATC CAACAGATCC ATATCCACAA 8330       8340       8350       8360
    GGACCGGGGA CAGCCAGCCA ACGAAGAAAC AGAAGAAGAC 8370       8380       8390       8400
    GGTGGAAGCA ACGGTGGAGA CAGATACTGG CCCTGGCCGA 8410       8420       8430       8440
    TAGCATATAT ACATTTCCTG ATCCGCCAGC TGATTCGCCT 8450       8460       8470       8480
    CTTGACCAGA CTATACAGCA TCTGCAGGGA CTTACTATCC 8490       8500       8510       8520
    AGGAGCTTCC TGACCCTCCA ACTCATCTAC CAGAATCTCA 8530       8540       8550       8560
    GAGACTGGCT GAGACTTAGA ACAGCCTTCT TGCAATATGG 8570       8580       8590       8600
    GTGCGAGTGG ATCCAAGAAG CATTCCAGGC CGCCGCGAGG 8610       8620       8630       8640
    GCTACAAGAG AGACTCTTGC GGGCGCGTGC AGGGGCTTGT 8650       8660       8670       8680
    GGAGGGTATT GGAACGAATC GGGAGGGGAA TACTCGCGGT 8690       8700       8710       8720
    TCCAAGAAGG ATCAGACAGG GAGCACAAAT CGCCCTCCTG 8730       8740       8750       8760
    TGAGGGACGG CAGTATCAGC AGGGAGACTT TATGAATACT 8770       8780       8790       8800
    CCATGGAAGG ACCCAGCAGC AGAAAGGGAG AAAAATTTGT 8810       8820       8830       8840
    ACAGGCAACA AAATATGGAT GATGTAGATT CAGATGATGA 8850       8860       8870       8880
    TGACCAAGTA AGAGTTTCTG TCACACCAAA AGTACCACTA 8890       8800       8910       8920
    AGACCAATGA CACATAGATT GGCAATAGAT ATGTCACATT 8930       8940       8950       8960
    TAATAAAAAC AAGGGGGGGA CTGGAAGGGA TGTTTTACAG 8970       8980       8990       9000
    TGAAAGAAGA CATAAAATCT TAAATATATA CTTAGAAAAG 9010       9020       9030       9040
    GAAGAAGGGA TAATTGCAGA TTGGCAGAAC TACACTCATG 9050       9060       9070       9080
    GGCCAGGAGT AAGATACCCA ATGTTCTTTG GGTGGCTATG 9090       9100       9110       9120
    GAAGCTAGTA CCAGTAGATG TCCCACAAGA AGGGGAGGAC 9130       9140       9150       9160
    ACTGAGACTC ACTGCTTAGT ACATCCAGCA CAAACAAGCA 9170       9180       9190       9200
    AGTTTGATGA CCCGCATGGG GAGACACTAG TCTGGGAGTT 9210       9220       9230       9240
    TGATCCCTTG CTGGCTTATA GTTACGAGGC TTTTATTCGG 9250       9260       9270       9280
    TACCCAGAGG AATTTGGGCA CAAGTCAGGC CTGCCAGAGG 9290       9300       9310       9320
```

-continued

```
AAGAGTGGAA GGCGAGACTG AAAGCAAGAG GAATACCATT 9330       9340       9350       9360
TAGTTAAAGA CAGGAACAGC TATACTTGGT CAGGGCAGGA 9370       9380       9390       9400
AGTAACTAAC AGAAACAGCT GAGACTGCAG GGACTTTCCA 9410       9420       9430       9440
GAAGGGGCTG TAACCAAGGG AGGGACATGG GAGGAGCTGG 9450       9460       9470       9480
TGGGGAACGC CCTCATATTC TCTGTATAAA TATACCCGCT 9490       9500       9510       9520
AGCTTGCATT GTACTTCGGT CGCTCTGCGG AGAGGCTGGC 9530       9540       9550       9560
```

-continued

```
AGATTGAGCC CTGGGAGGTT CTCTCCAGCA GTAGCAGGTA 9570       9580       9590       9600
GAGCCTGGGT GTTCCCTGCT AGACTCTCAA CAGCACTTGG 9610       9620       9630       9640
CCGGTGCTGG GCAGACGGCC CCACGCTTGC TTGCTTAAAA 9650       9660       9670
ACCTCCTTAA TAAAGCTGCC AGTTAGAAGC A.
```

2. An isolated and purified DNA segment having the nucleotide sequence or a nucleotide sequence encoding one or more of the amino acid sequences as shown in the following sequence:

```
GGTCGCTCTGCGGAGAGGCTGGCAGATTGAGCCCTGGGAGGTTCTCTCCAGCACTAGCAG
                  .         .         .         .         .         .
GTAGAGCCTGGGTGTTCCCTGCTAGACTCTCACCAGCACTTGGCCGGTGCTGGGCAGACG
                  .         .         .        100         .         .
GCCCCACGCTTGCTTGCTTAAAAACCTCTTAATAAAGCTGCCAGTTAGAAGCAAGTTAAG
                  .         .         .         .         .         .
TGTGTGCTCCCATCTCTCCTAGTCGCCGCCTGGTCATTCGGTGTTCACCTGAGTAACAAG
                  .         .        200         .         .         .
ACCCTGGTCTGTTAGGACCCTTCTTGCTTTGGGAAACCGAGGCAGGAAAATCCCTAGCAG
                  .         .         .         .         .        300
GTTGGCGCCTGAACAGGGACTTGAAGAAGACTGAGAAGTCTTGGAACACGGCTGACTGAA
                  .         .         .         .         .         .
GGCAGTAAGGGCGGCAGGAACAAACCACGACGGAGTGCTCCTAGAAAGGCGCGGGCCGAG
                  .         .         .        400         .         .
GTACCAAAGGCAGCGTGTGGAGCGGGAGGAGAAGAGGCCTCCGGGTGAAGGTAAGTACCT
                  .         .         .         .         .         .
ACACCAAAAACTGTAGCCGAAAGGGCTTGCTATCCTACCTTTAGACAGGTAGAAGATTGT
                  .        500         .         .         .         .
    MetGlyAlaArgAsnSerValLeuArgGlyLysLysAlaAspGluLeuGluArgIle
GGGAGATGGGCGCGAGAAACTCCGTCTTGAGAGGGAAAAAAGCAGATGAATTAGAAAGAA
                  .         .         .         .         .        600
     ArgLeuArgProGlyGlyLysLysLysTyrArgLeuLysHisIleValTrpAlaAlaAsn
TCAGGTTACGGCCCGGCGGAAAGAAAAAGTACAGGCTAAAACATATTGTGTGGGCAGCGA
                  .         .         .         .         .         .
         LysLeuAspArgPheGlyLeuAlaGluSerLeuLeuGluSerLysGluGlyCysGlnLys
ATAAATTGGACAGATTCGGATTACCAGAGAGCCTGTTGGAGTCAAAAGAGGGTTGTCAAA
                  .         .         .        700         .         .
    IleLeuThrValLeuAspProMetValProThrGlySerGluAsnLeuLysSerLeuPhe
AAATTCTTACAGTTTTAGATCCAATGGTACCGACAGGTTCAGAAAATTTAAAAAGTCTTT
                  .         .         .         .         .         .
    AsnThrValCysValIleTrpCysIleHisAlaGluGluLysValLysAspThrGluGly
TTAATACTGTCTGCGTCATTTGGTGCATACACGCAGAAGAGAAAGTGAAAGATACTGAAG
                  .         .        800         .         .         .
   AlaLysGlnIleValArgArgHisLeuValAlaGluThrGlyThrAlaGluLysMetPro
GAGCAAAACAAATAGTGCGGAGACATCTAGTGGCAGAAACAGGAACTGCAGAGAAAATGC
                  .         .         .         .         .        900
   SerThrSerArgProThrAlaProSerSerGluLysGlyGlyAsnTyrProValGlnHis
CAAGCACAAGTAGACCAACAGCACCATCTAGCGAGAAGGGAGGAAATTACCCAGTGCAAC
                  .         .         .         .         .         .
  ValGlyGlyAsnTyrThrHisIleProLeuSerProArgThrLeuAsnAlaTrpValLys
ATGTAGGCGGCAACTACACCCATATACCGCTGAGTCCCCGAACCCTAAATGCCTGGGTAA
                  .         .         .       1000         .         .
  LeuValGluGluLysLysPheGlyAlaGluValValProGlyPheGlnAlaLeuSerGlu
AATTAGTAGAGGAAAAAAAGTTCGGGGCAGAAGTAGTGCCAGGATTTCAGGCACTCTCAG
                  .         .         .         .         .         .
  GlyCysThrProTyrAspIleAsnGlnMetLeuAsnCysValGlyAspHisGlnAlaAla
AAGGCTGCACGCCCTATGATATCAACCAAATGCTTAATTGTGTGGGCGACCATCAAGCAG
                  .         .       1100         .         .         .
  MetGlnIleIleArgGluIleIleAsnGluGluAlaAlaGluTrpAspValGlnLisPro
CCATGCAGATAATCAGGGAGATTATCAATGAGGAAGCAGCAGAATGGGATGTGCAACATC
                  .         .         .         .         .       1200
  IleProGlyProLeuProAlaGlyGlnLeuArgGluProArgGlySerAspIleAlaGly
CAATACCAGGCCCCTTACCAGCGGGGCAGCTTAGAGAGCCAAGGGGATCTGACATAGCAG
                  .         .         .         .         .         .
   ThrThrSerThrValGluGluGlnIleGlnTrpMetPheArgProGlnAsnProValPro
CGACAACAAGCACAGTAGAAGAACAGATCCAGTGGATGTTTAGGCCACAAAATCCTGTAC
```

```
                                1300
   ValGlyAsnIleTyrArgArgTrpIleGlnIleGlyLeuGlnLysCysValArgMetTyr
   CAGTAGGAAACATCTATAGAAGATGGATCCAGATAGGATTGCAGAAGTGTGTCAGGATGT

AsnProThrAsnIleLeuAspIleLysGlnGlyProLysGluProPheGlnSerTyrVal
   ACAACCCGACCAACATCCTAGACATAAAACAGGGACCAAAGGAGCCGTTCCAAAGCTATG
                  1400
   AspArgPheTyrLysSerLeuArgAlaGluGlnThrAspProAlaValLysAsnTrpMet
   TAGATAGATTCTACAAAAGCTTGAGGGCAGAACAAACAGATCCAGCAGTGAAGAATTGGA
                                                        1500
   ThrGlnThrLeuLeuValGlnAsnAlaAsnProAspCysLysLeuValLeuLysGlyLeu
   TGACCCAAACACTGCTAGTACAAAATGCCAACCCAGACTGTAAATTAGTGCTAAAAGGAC

GlyMetAsnProThrLeuGluGluMetLeuThrAlaCysGlnGlyValGlyGlyProGly
   TAGGGATGAACCCTACCTTAGAAGAGATGCTGACCGCCTGTCAGGGGGTAGGTGGGCCAG
                                  1600
   GlnLysAlaArgLeuMetAlaGluAlaLeuLysGluValIleGlyProAlaProIlePro
   GCCAGAAAGCTAGATTAATGGCAGAGGCCCTGAAAGAGGTCATAGGACCTGCCCCTATCC

PheAlaAlaAlaGlnGlnArgLysAlaPheLysCysTrpAsnCysGlyLysGluGlyHis
   CATTCGCAGCAGCCCAGCAGAGAAAGGCATTTAAATGCTGGAACTGTGGAAAGGAAGGGC
                 1700
   SerAlaArgGlnCysArgAlaProArgArgGlnGlyCysTrpLysCysGlyLysProGly
   ACTCGGCAAGACAATGCCGAGCACCTAGAAGGCAGGGCTGCTGGAAGTGTGGTAAGCCAG
                                                      1800
                       ThrGlyArgPhePheArgThrGlyProLeuGly
   HisIleMetThrAsnCysProAspArgGlnAlaGlyPheLeuGlyLeuGlyProTrpGly
   GACACATCATGAGAAACTGCCCAGATAGACAGGCAGGTTTTTTAGGACTGGGCCCTTGGG

LysGluAlaProGlnLeuProArgGlyProSerSerAlaGlyAlaAspThrAsnSerThr
   LysLysProArgAsnPheProValAlaGlnValProGlnGlyLeuThrProThrAlaPro
   GAAAGAAGCCGCGCAACTTCCCCGTGGCCCAAGTTCCGCAGGGGCTGACACCAACAGCAC
                              1900
   ProSerGlySerSerSerGlySerThrGlyGluIleTyrAlaAlaArgGluLysThrGlu
   ProValAspProAlaValAspLeuLeuGluLysTyrMetGlnGlnGlyLysArgGlnArg
   CCCCAGTGGATCCAGCAGTGGATCTACTGGAGAAATATATGCAGCAAGGGAAAAGACAGA

ArgAlaGluArgGluThrIleGlnGlySerAspArgGlyLeuThrAlaProArgAlaGly
   GluGlnArgGluArgProTyrLysGluValThrGluAspLeuLeuHisLeuGluGlnGly
   GAGAGCAGAGAGAGAGACCATACAAGGAAGTGACAGAGGACTTACTGCACCTCGAGCAGG
                    2000
   GlyAspThrIleGlnGlyAlaThrAsnArgGlyLeuAlaAlaProGlnPheSerLeuTrp
   GluThrProTyrArgGluProProThrGluAspLeuLeuHisLeuAsnSerLeuPheGly
   GGGAGACACCATACAGGGAGCCACCAACGAGGACTTGCTGCACCTCAATTCTCTCTTTG
                                                      2100
   LysArgProValValThrAlaTyrIleGluGlyGlnProValGluValLeuLeuAspThr
   LysAspGln
   GAAAAGACCAGTAGTCACAGCATACATTGAGGGTCAGCCAGTAGAAGTCTTGTTAGACAC

GlyAlaAspAspSerIleValAlaGlyIleGluLeuGlyAsnAsnTyrSerProLysIle
   AGGGGCTGACGACTCAATAGTAGCAGGAATAGAGTTAGGGAACAATTATAGCCCAAAAAT
                                  2200
   ValGlyGlyIleGlyGlyPheIleAsnThrLysGluTyrLysAsnValGluIleGluVal
   AGTAGGGGGAATAGGGGGATTCATAAATACCAAGGAATATAAAAATGTAGAAATAGAAGT

LeuAsnLysLysValArgAlaThrIleMetThrGlyAspThrProIleAsnIlePheGly
   TCTAAATAAAAAGGTACGGGCCACCATAATGACAGGCGACACCCCAATCAACATTTTTGG
                      2300
   ArgAsnIleLeuThrAlaLeuGlyMetSerLeuAsnLeuProValAlaLysValGluPro
   CAGAAATATTCTGACAGCCTTAGGCATGTCATTAAATCTACCAGTCGCCAAAGTAGAGCC
                                                      2400
   IleLysIleMetLeuLysProGlyLysAspGlyProLeuArgGlnTrpProLeuThr
   AATAAAAATAATGCTAAAGCCAGGGAAAGATGGACCAAAACTGAGACAATGGCCCTTAAC

LysGluLysIleGluAlaLeuLysGluIleCysGluLysMetGluLysGluGlyGlnLeu
   AAAAGAAAAAATAGAAGCACTAAAAGAAATCTGTGAAAAAATGGAAAAAGAAGGCCAGCT
                                 2500
   GluGluAlaProProThrAsnProTyrAsnThrProThrPheAlaIleLysLysLysAsp
   AGAGGAAGCACCTCCAACTAATCCTTATAATACCCCCACATTTGCAATCAAGAAAAAGGA

LysAsnLysTrpArgMetLeuIleAspPheArgGluLeuAsnLysValThrGlnAspPhe
   CAAAAACAAATGGAGGATGCTAATAGATTTCAGAGAACTAAACAAGGTAACTCAAGATTT
                    2600
   ThrGluIleGlnLeuGlyIleProHisProAlaGlyLeuAlaLysLysArgArgIleThr
   CACAGAAATTCAGTTAGGAATTCCACACCCAGCAGGGTTGGCCAAGAAGAGAAGAATTAC
                                                      2700
   ValLeuAspValGlyAspAlaTyrPheSerIleProLeuHisGluAspPheArgProTyr
   TGTACTAGATGTAGGGGATGCTTACTTTTCCATACCACTACATGAGGACTTTAGACCATA

ThrAlaPheThrLeuProSerValAsnAsnAlaGluProGlyLysArgTyrIleTyrLys
```

-continued

```
TACTGCATTTACTCTACCATCAGTGAACAATGCAGAACCAGGAAAAAGATACATATATAA
                         .         .         2800        .         .
   ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT
    .         .         .         .         .         .
    LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
              .         2900        .         .         .
   LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
    .         .         .         .         3000        .
   LeuLeuAsnGlyLeuGlyPheSerThrProAspGluLysPheGlnLysAspProProTyr
ACTTCTAAATGGCCTAGGATTTTCTACCCCAGATGAGAAGTTCCAAAAAGACCCTCCATA
    .         .         .         .         .         .
   HisTrpMetGlyTyrGluLeuTrpProThrLysTrpLysLeuGlnLysIleGlnLeuPro
CCACTGGATGGGCTATGAACTATGGCCAACTAAATGGAAGTTGCAGAAAATACAGTTGCC
    .         .         3100        .         .         .
    GlnLysGluIleTrpThrValAsnAspIleGlnLysLeuValGlyValLeuAsnTrpAla
CCAAAAAGAAATATGGACAGTCAATGACATCCAGAAGCTAGTGGGTGTCCTAAATTGGGC
    .         .         .         .         .         .
    AlaGlnLeuTyrProGlyIleLysThrLysHisLeuCysArgLeuIleArgGlyLysMet
AGCACAACTCTACCCAGGGATAAAGACCAAACACTTATGTAGGTTAATCAGAGGAAAAAT
         .         3200        .         .         .         .
   ThrLeuThrGluGluValGlnTrpThrGluLeuAlaGluAlaGluLeuGluGluAsnArg
GACACTCACAGAAGAAGTACAGTGGACAGAATTACCAGAAGCAGAGCTAGAAGAAAACAG
    .         .         .         .         .         3300
    IleIleLeuSerGlnGluGlnGluGlyHisTyrTyrGlnGluGluLysGluLeuGluAla
AATTATCCTAAGCCAGGAACAAGAGGGACACTATTACCAAGAAGAAAAAGAGCTAGAAGC
    .         .         .         .         .         .
    ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
              .         3400        .         .         .
   LeuLysValGlyLysTyrAlaLysValLysAsnThrHisThrAsnGlyIleArgLeuLeu
TCTAAAAGTAGGAAAATATGCAAAGGTGAAAAACACCCATACCAATGGAATCAGATTGTT
    .         .         .         .         .         .
    AlaGlnValValGlnLysIleGlyLysGluAlaLeuValIleTrpGlyArgIleProLys
AGCACAGGTAGTTCAGAAAATAGGAAAAGAAGCACTAGTCATTTGGGGACCAATACCAAA
         .         3500        .         .         .         .
    PheHisLeuProValGluArgGluIleTrpGluGlnTrpTrpAspAsnTyrTrpGlnVal
ATTTCACCTACCAGTAGAGAGAGAAATCTGGGAGCAGTGGTGGGATAACTACTGGCAAGT
    .         .         .         .         .         3600
    ThrTrpIleProAspTrpAspPheValSerThrProProLeuValArgLeuAlaPheAsn
GACATGGATCCCAGACTGGGACTTCGTGTCTACCCCACCACTGGTCAGGTTAGCGTTTAA
    .         .         .         .         .         .
   LeuValGlySerAspProIleProGlyAlaGluThrPheTyrThrAspGlySerCysAsnArg
CCTGGTAGGGGATCCTATACCAGGTGCAGAGACCTTCTACACAGATCGATCCTGCAATAG
         .         3700        .         .         .         .
    GlnSerLysGluGlyLysAlaGlyTyrValThrAspArgGlyLysAspLysValLysLys
GCAATCAAAAGAAGGAAAAGCAGGATATGTAACAGATAGAGGGAAAGACAAGGTAAAGAA
    .         .         .         .         .         .
   LeuGluGlnThrThrAsnGlnGlnAlaGluLeuGluAlaPheAlaMetAlaLeuThrAsp
ACTAGAGCAAACTACCAATCAGCAAGCAGAACTAGAAGCCTTTGCGATGGCACTAACAGA
    .         .         3800        .         .         .
    SerGlyProLysValAsnIleIleValAspSerGlnTyrValMetGlyIleSerAlaSer
CTCGGGTCCAAAAGTTAATATTATAGTAGACTCACAGTATGTAATGGGGATCAGTGCAAG
    .         .         .         .         .         3900
   GlnProThrGluSerGluSerLysIleValAsnGlnIleIleGluGluMetIleLysLys
CCAACCAACAGAGTCAGAAAGTAAAATAGTGAACCAGATCATAGAAGAAATGATAAAAAA
    .         .         .         .         .         .
   GluAlaIleTyrValAlaTrpValProAlaHisLysGlyIleGlyGlyAsnGlnGluVal
GGAAGCAATCTATGTTGCATGGGTCCCAGCCCACAAAGGCATAGGGGGAAACCAGGAAGT
                        .         4000        .         .
    AspHisLeuValSerGlnGlyIleArgGlnValLeuPheLeuGluLysIleGluProAla
AGATCATTTAGTGAGTCAGGGTATCAGACAAGTGTTGTTCCTGGAAAAAATAGAGCCCGC
    .         .         .         .         .         .
    GlnGluGluHisGluLysTyrHisSerAsnValLysGluLeuSerHisLysPheGlyIle
TCAGGAAGAACATGAAAAATATCATAGCAATGTAAAAGAACTGTCTCATAAATTTGGAAT
         .         4100        .         .         .         .
    ProAsnLeuValAlaArgGlnIleValAsnSerCysAlaGlnCysGlnGlnLysGlyGlu
ACCCAATTTAGTGGCAAGGCAAATAGTAAACTCATGTGCCCAATGTCAACAGAAAGGGGA
    .         .         .         .         .         4200
    AlaIleHisGlyGlnValAsnAlaGluLeuGlyThrTrpGlnMetAspCysThrHisLeu
AGCTATACATGGGCAAGTAAATGCAGAACTAGCCACTTGGCAAATGGACTGCACACATTT
    .         .         .         .         .         .
    GluGlyLysIleIleIleValAlaAlaValHisValAlaSerGlyPheIleGluAlaGluVal
AGAAGGAAAGATCATTATAGTAGCAGTACATGTTGCAAGTGGATTTATAGAAGCAGAAGT
                        .         4300        .         .
   IleProGlnGluSerGlyArgGlnThrAlaLeuPheLeuLeuLysLeuAlaSerArgTrp
CATCGCACAGGAATCAGGAAGACAAACAGCACTCTTCCTATTGAAACTGGCAAGTAGGTG
    .         .         .         .         .         .
```

-continued

```
ProIleThrHisLeuHisThrAspAsnGlyAlaAsnPheThrSerGlnGluValLysMet
GCCAATAACACACTTGCATACAGATAATGGTGCCAACTTCACTTCACAGGAGGTGAAGAT
                         .         4400           .            .
        ValAlaTrpTrpIleGlyIleGluGlnSerPheGlyValProTyrAsnProGlnSerGln
GGTAGCATGGTGGATAGGTATAGAACAATCCTTTGGAGTACCTTACAATCCACAGAGCCA
         .              .               .               .        4500
        GlyValValGluAlaMetAsnHisHisLeuLysAsnGluIleSerArgIleArgGluGln
AGGAGTAGTAGAAGCAATGAATCACCATCTAAAAAACCAAATAAGTAGAATCAGAGAACA
         .              .               .               .               .
         AlaAsnThrIleGluThrIleValLeuMetAlaIleHisCysMetAsnPheLysArgArg
GGCAAATACAATAGAAACAATAGTACTAATGGCAATTCATTGCATGAATTTTAAAAGAAG
         .              .         4600           .               .
         GlyGlyIleGlyAspMetThrProSerGluArgLeuIleAsnMetIleThrThrGluGln
GGGGGGAATAGGGGATATGACTCCATCAGAAAGATTAATCAATATGATCACCACAGAACA
         .              .               .               .               .
         GluIleGlnPheLeuGlnAlaLysAsnSerLysLeuLysAspPheArgValTyrPheArg
AGAGATACAATTCCTCCAAGCCAAAAATTCAAAATTAAAAGATTTTCGGGTCTATTTCAG
                         .         4700           .               .
         GluGlyArgAspGlnLeuTrpLysGlyProGlyGluLeuLeuTrpLysGlyGluGlyAla
AGAAGGCAGACATCAGTTGTGGAAAGGACCTGGGGAACTACTGTGGAAAGGAGAAGGAGC
         .              .               .               .        4800
         ValLeuValLysValGlyThrAspIleLysIleIleProArgArgLysAlaLysIleIle
AGTCCTAGTCAAGGTAGGAACAGACATAAAAATAATACCAAGAAGGAAAGCCAAGATCAT
         .              .               .               .               .
         ArgAspTyrGlyGlyArgGlnGluMetAspSerGlySerHisLeuGluGlyAlaArgGlu
                MetGluGluAspLysArgTrpIleValValProThrTrpArgValProGlyArg
CAGACACTATGGAGGAAGACAAGAGATGGATAGTGGTTCCCACCTGGAGGGTGCCAGGGA
         .              .         4900           .               .
AspGlyGluMetAla
         MetGluLysTrpHisSerLeuValLysTyrLeuLysTyrLysThrLysAspLeuGluLys
GGATGGAGAAATGGCATAGCCTTGTCAAGTATCTAAAATACAAAACAAAGGATCTAGAAA
         .              .               .               .               .
         ValCysTyrValProHisHisLysValGlyTrpAlaTrpTrpThrCysSerArgValIle
AGGTGTGCTATGTTCCCCACCATAAGGTGGGATGGGCATGGTGGACTTGCAGCAGGGTAA
         .              .         5000           .               .
         PheProLeuLysGlyAsnSerHisLeuGluIleGlnAlaTyrTrpAsnLeuThrProGlu
TATTCCCATTAAAAGGAAACAGTCATCTAGAGATACAGGCATATTGGAACTTAACACCAG
         .              .               .               .        5100
         LysGlyTrpLeuSerSerTyrSerValArgIleThrTrpTyrThrGluLysPheTrpThr
AAAAAGGATGGCTCTCCTCTTATTCAGTAAGAATAACTTGGTACACAGAAAAGTTCTGGA
         .              .               .               .               .
         AspValThrProAspCysAlaAspValLeuIleHisSerThrTyrPheProCysPheThr
CAGATGTTACCCCAGACTGTGCAGATGTCCTAATACATAGCACTTATTTCCCTTGCTTTA
                         .         5200           .               .
         AlaGlyGluValArgArgAlaIleArgGlyGluLysLeuLeuSerCysCysAsnTyrPro
CAGCAGGTGAAGTAAGAAGAGCCATCAGAGGGGAAAAGTTATTGTCCTGCTGCAATTATC
         .              .               .               .               .
         ArgAlaHisArgAlaGlnValProSerLeuGlnPheLeuAlaLeuValValValGlnGln
CCCGAGCTCATAGACCCCAGGTACCGTCACTTCAATTTCTGGCCTTAGTGGTAGTCCAAC
         .              .         5300           .               .
         MetThrAspProArgGluThrValProProGlyAsnSerGlyGluGluThrIleGly
         AsnAspArgProGlnArgAspSerThrThrArgLysGlnArgArgArgAspTyrArgArg
AAAATGACAGACCCCAGAGAGACAGTACCACCAGGAAACAGCGGCGAAGAGACTATCGGA
         .              .               .               .        5400
         GluAlaPheAlaTrpLeuAsnArgThrValGluAlaIleAsnArgGluAlaValAsnHis
            GlyLeuArgLeuAlaLysGlnAspSerArgSerHisLysGlnArgSerSerGluSerPro
GAGGCCTTCGCCTGGCTAAACAGGACAGTAGAAGCCATAAACAGAGAAGCAGTGAATCAC
         .              .               .               .               .
         LeuProArgGluLeuIlePheGlnValTrpGlnArgSerTrpArgTyrTrpHisAspGlu
            ThrProArgThrTyrPheProGlyValAlaGluValLeuGluIleLeuAla
CTACCCCGAGAACTTATTTTCCAGGTGTGGCAGAGGTCCTGGAGATACTGGCATGATGAA
                         .         5500           .               .
         GlnGlyMetSerGluSerTyrThrLysTyrArgTyrLeuCysIleIleGlnLysAlaVal
CAAGGGATGTCAGAAAGTTACACAAAGTATAGATATTTGTGCATAATACAGAAAGCAGTG
         .              .               .               .               .
         TyrMetHisValArgLysGlyCysThrCysLeuGlyArgGlyHisGlyProGlyGlyTrp
TACATGCATGTTAGGAAAGGGTGTACTTGCCTGGGGAGGGGACATGGGCCAGGAGGGTGG
         .              .         5600           .               .
ArgProGlyProProProProProProProGlyLeuVal
                                                MetAlaGluAlaProThrGlu
AGACCAGGGCCTCCTCCTCCTCCCCCTCCAGGTCTGGTCTAATGGCTGAAGCACCAACAG
         .              .               .               .        5700
         LeuProProValAspGlyThrProLeuArgGluProGlyAspGluTrpIleIleGluIle
AGCTCCCCCCGGTGGATGGGACCCCACTGAGGGAGCCAGGGGATGAGTGGATAATAGAAA
         .              .               .               .               .
         LeuArgGluIleLysGluGluAlaLeuLysHisPheAspProArgLeuLeuIleAlaLeu
TCTTGAGAGAAATAAAAGAAGAAGCTTTAAAGCATTTTGACCCTCGCTTGCTAATTGCGC
                         .         5800           .               .
                                       MetGluThrProLeuLysAlaProGluSerSerLeu
         GlyLysTyrIleTyrThrArgHisGlyAspThrLeuGluGlyAlaArgGluLeuIleLys
```

-continued

```
TTGGCAAATATATCTATACTAGACATGGAGACACCCTTGAAGGCGCCAGAGAGCTCATTA
LysSerCysAsnGluProPheSerArgThrSerGluGlnAspValAlaThrGlnGluLeu
  ValLeuGlnArgAlaLeuPheThrHisPheArgAlaGlyCysGlyHisSerArgIleGly
AAGTCCTGCAACGAGCCCTTTTCACGCACTTCAGAGCAGGATGTGGCCACTCAAGAATTG
     .           5900          .           .           .
AlaArgGlnGlyGluGluIleLeuSerGlnLeuTyrArgProLeuGluThrCysAsnAsn
  GlnThrArgGlyGlyAsnProLeuSerAlaIleProThrProArgAsnMetGln
GCCAGACAAGGGGAGGAAATCCTCTCTCAGCTATACCGACCCCTAGAAACATGCAATAAC
     .           .           .           .           6000
SerCysTyrCysLysArgCycCysTyrHisCysGlnMetCysPheLeuAsnLysGlyLeu
TCATGCTATTGTAAGCGATGCTGCTACCATTGTCAGATGTGTTTTCTAAACAAGGGGCTC
     .           .           .           .           .
GlyIleCysTyrGluArgLysGlyArgArgArgArgThrProLysLysThrLysThrHis
        MetAsnGluArgAlaAspGluGluGlyLeuGlnArgLysLeuArgLeuIle
GGGATATGTTATGAACGAAAGGGCAGACGAAGAAGGACTCCAAAGAAAACTAAGACTCAT
     .           .           .           6100          .           .
ProSerProThrProAspLys
  ArgLeuLeuHisGlnThr
                        MetMetAsnGlnLeuLeuIleAlaIleLeuLeuAla
CCGTCTCCTACACCAGACAAGTGAGTATGATGAATCAGCTGCTTATTGCCATTTTATTAG
     .           .           .           .           .
   SerAlaCysLeuValTyrCysThrGlnTyrValThrValPheTyrGlyValProThrTrp
CTAGTGCTTGCTTAGTATATTGCACCCAATATGTAACTGTTTTCTATGGCGTACCCACGT
     .           6200          .           .           .
   LysAsnAlaThrIleProLeuPheCysAlaThrArgAsnArgAspThrTrpGlyThrIle
GGAAAAATGCAACCATTCCCCTCTTTTGTGCAACCAGAAATAGGGATACTTGGGGAACCA
     .           .           .           .           6300
   GlnCysLeuProAspAsnAspAspTyrGlnGluIleThrLeuAsnValThrGluAlaPhe
TACAGTGCTTGCCTGACAATGATGATTATCAGGAAATAACTTTGAATGTAACAGAGCCTT
     .           .           .           .           .
   AspAlaTrpAsnAsnThrValThrGluGlnAlaIleGluAspValTrpHisLeuPheGlu
TTGATGCATGGAATAATACAGTAACAGAACAAGCAATAGAAGATGTCTGGCATCTATTCG
     .           .           .           6400          .
   ThrSerIleLysProCysValLysLeuThrProLeuCysValAlaMetLysCysSerSer
AGACATCAATAAAACCATGTGTCAAACTAACACCTTTATGTGTAGCAATGAAATGCAGCA
     .           .           .           .           .
   ThrGluSerSerThrGlyAsnAsnThrThrSerLysSerThrSerThrThrThrThrThr
GCACAGAGAGCAGCACAGGGAACAACACAACCTCAAAGAGCACAAGCACAACCACAACCA
     .           6500          .           .           .
   ProThrAspGlnGluGlnIleSerGluAspThrProCysAlaArgAlaAspAsnCys
CACCCACAGACCAGGAGCAAGAGATAAGTGAGGATACTCCATGCGCACGCGCAGACAACT
     .           .           .           .           6600
   SerGlyLeuGlyGluGluGluThrIleAsnCysGlnPheAsnMetThrGlyLeuGluArg
GCTCAGGATTGGGAGAGGAAGAAACGATCAATTGCCAGTTCAATATGACAGGATTAGAAA
     .           .           .           .           .
   AspLysLysLysGlnTyrAsnGluThrTrpTyrSerLysAspValValCysGluThrAsn
GAGATAAGAAAAAACAGTATAATGAAACATGGTACTCAAAAGATGTGGTTTGTGAGACAA
     .           .           .           6700          .
   AsnSerThrAsnGlnThrGlnCysTyrMetAsnHisCysAsnThrSerValIleThrGlu
ATAATAGCACAAATCAGACCCAGTGTTACATGAACCATTGCAACACATCAGTCATCACAG
     .           .           .           .           .
   SerCysAspLysHisTyrTrpAspAlaIleArgPheArgTyrCysAlaProProGlyTyr
AATCATGTGACAAGCACTATTGGGATGCTATAAGGTTTAGATACTGTGCACCACCGGGTT
     .           6800          .           .           .
   AlaLeuLeuArgCysAsnAspThrAsnTyrSerGlyPheAlaProAsnCysSerLysVal
ATGCCCTATTAAGATGTAATGATACCAATTATTCAGGCTTTGCACCCAACTGTTCTAAAG
     .           .           .           .           6900
   ValAlaSerThrCysThrArgMetMetGluThrGlnThrSerThrTrpPheGlyPheAsn
TAGTAGCTTCTACATGCACCAGGATGATGGAAACGCAAACTTCCACATGGTTTGGCTTTA
     .           .           .           .           .
   GlyThrArgAlaGluAsnArgThrTyrIleTyrTrpHisGlyArgAspAsnArgThrIle
ATGGCACTAGAGCAGAGAATAGAACATATATCTATTGGCATGGCAGAGATAATAGAACTA
     .           .           .           7000          .           .
   IleSerLeuAsnLysTyrTyrAsnLeuSerLeuHisCysLysArgProGlyAsnLysThr
TCATCAGCTTAAACAAATATTATAATCTCAGTTTGCATTGTAAGAGGCCAGGGAATAAGA
     .           .           .           .           .
   ValLysGlnIleMetLeuMetSerGlyHisValPheHisSerHisTyrGlnProIleAsn
CAGTGAAACAAATAATGCTTATGTCAGGACATGTGTTTCACTCCCACTACCAGCCGATCA
     .           7100          .           .           .
   LysArgProArgGlnAlaTrpCysTrpPheLysGlyLysTrpLysAspAlaMetGlnGlu
ATAAAAGACCCAGACAAGCATGGTGCTGGTTCAAAGGCAAATGGAAAGACGCCATGCAGG
     .           .           .           .           7200
   ValLysGluThrLeuAlaLysHisProArgTyrArgGlyThrAsnAspThrArgAsnIle
AGGTGAAGGAAACCCTTGCAAAACATCCCAGGTATAGAGGAACCAATGACACAAGGAATA
     .           .           .           .           .
   SerPheAlaAlaProGlyLysGlySerAspProGluValAlaTyrMetTrpThrAsnCys
TTAGCTTTGCAGCGCCAGGAAAAGGCTCAGACCCAGAAGTAGCATACATGTGGACTAACT
     .           .           .           7300          .           .
   ArgGlyGluPheLeuTyrCysAsnMetThrTrpPheLeuAsnTrpIleGluAsnLysThr
```

-continued

```
GCAGAGGAGAGTTTCTCTACTGCAACATGACTTGGTTCCTCAATTGGATAGAGAATAAGA
    HisArgAsnTyrAlaProCysHisIleLysGlnIleIleAsnThrTrpHisLysValGly
CACACCGCAATTATGCACCGTGCCATATAAAGCAAATAATTAACACATGGCATAAGGTAG
              .         7400        .         .         .
    ArgAsnValTyrLeuProProArgGluGlyGluLeuSerCysAsnSerThrValThrSer
GGAGAAATGTATATTTGCCTCCCAGGGAAGGGGAGCTGTCCTGCAACTCAACAGTAACCA
    .         .         .         .         .         7500
    IleIleAlaAsnIleAspTrpGlnAsnAsnAsnGlnThrAsnIleThrPheSerAlaGlu
GCATAATTGCTAACATTGACTGGCAAAACAATAATCAGACAAACATTACCTTTAGTGCAG
    .         .         .         .         .         .
    ValAlaGluLeuTyrArgLeuGluLeuGlyAspTyrLysLeuValGluIleThrProIle
AGGTGGCAGAACTATACAGATTGGAGTTGGGAGATTATAAATTGGTAGAAATAACACCAA
    .         .         .         7600        .         .
    GlyPheAlaProThrLysGluLysArgTyrSerSerAlaHisGlyArgHisThrArgGly
TTGGCTTCGCACCTACAAAAGAAAAAAGATACTCCTCTGCTCACGGGAGACATACAAGAG
    .         .         .         .         .         .
    ValPheValLeuGlyPheLeuGlyPheLeuAlaThrAlaGlySerAlaMetGlyAlaAla
GTGTGTTCGTGCTAGGGTTCTTGGGTTTTCTCGCAACAGCAGGTTCTGCAATGGGCGCGG
    .         7700        .         .         .         .
    SerLeuThrValSerAlaGlnSerArgThrLeuLeuAlaGlyIleValGlnGlnGlnGln
CGTCCCTGACCGTGTCGGCTCAGTCCCGGACTTTACTGGCCGGGATAGTGCAGCAACAGC
    .         .         .         .         .         7800
    GlnLeuLeuAspValValLysArgGlnGlnGluLeuLeuArgLeuThrValTrpGlyThr
AACAGCTGTTGGACGTGGTCAAGAGACAACAAGAACTGTTGCGACTGACCGTCTGGGGAA
    .         .         .         .         .         .
    LysAsnLeuGlnAlaArgValThrAlaIleGluLysTyrLeuGlnAspGlnAlaArgLeu
CGAAAAACCTCCAGGCAACAGTCACTGCTATAGAGAAGTACCTACAGGACCAGGCGCGGC
    .         .         .         .         .         7900
    AsnSerTrpGlyCysAlaPheArgGlnValCysHisThrThrValProTrpValAsnAsp
TAAATTCATGGGGATGTGCGTTTAGACAAGTCTGCCACACTACTGTACCATGGGTTAATG
    .         .         .         .         .         .
    SerLeuAlaProAspTrpAspAsnMetThrTrpGlnGluTrpGluLysGlnValArgTyr
ATTCCTTAGCACCTGACTGGGACAATATGACGTGGCAGGAATGGGAAAAACAAGTCCGCT
    .         8000        .         .         .         .
    LeuGluAlaAsnIleSerLysSerLeuGluGlnAlaGlnIleGlnGlnGluLysAsnMet
ACCTGGAGGCAAATATCAGTAAAAGTTTAGAACAGGCACAAATTCAGCAAGAGAAAAATA
    .         .         .         .         .         8100
    TyrGluLeuGlnLysLeuAsnSerTrpAspIlePheGlyAsnTrpPheAspLeuThrSer
TGTATGAACTACAAAAATTAAATAGCTGGGATATTTTTGGCAATTGGTTTGACTTAACCT
    .         .         .         .         .         .
    TrpValLysTyrIleGlnTyrGlyValLeuIleIleValAlaValIleAlaLeuArgIle
CCTGGGTCAAGTATATTCAATATGGAGTCCTTATAATAGTAGCAGTAATAGCTTTAACAA
    .         .         .         8200        .         .
    ValIleTyrValValGlnMetLeuSerArgLeuArgLysGlyTyrArgProValPheSer
TAGTGATATATGTAGTACAAATGTTAAGTAGGCTTAGAAAGGGCTATAGGCCTGTTTTCT
    .         .         .         .         .         .
                            SerIleSerThrArgThrGlyAspSerGlnPro
                        AsnProTyrProGlnGlyProGlyThrAlaSerGln
    SerProProGlyTyrIleGlnGlnIleHisIleHisLysAspArgGlyGlnProAlaAsn
CTTCCCCCCCCGGTTATATCCAACAGATCCATATCCACAAGGACCGGGGACAGCCAGCCA
    .         8300        .         .         .         .
ThrLysLysGlnLysLysThrValGluAlaThrValGluThrAspThrGlyProGlyArg
    ArgArgAsnArgArgArgArgTrpLysGlnArgTrpArgGlnIleLeuAlaLeuAlaAsp
    GluGluThrGluGluAspGlyGlySerAsnGlyGlyAspArgTyrTrpProTrpProIle
ACGAAGAAACAGAAGAAGACGGTGGAAGCAACGGTGGAGACAGATACTGGCCCTGGCCGA
    .         .         .         .         .         8400
    SerIleTyrThrPheProAspProProAlaAspSerProLeuAspGlnThrIleGlnHis
    AlaTyrIleHisPheLeuIleArgGlnLeuIleArgLeuLeuThrArgLeuTyrSerIle
TAGCATATATACATTTCCTGATCCGCCAGCTGATTCGCCTCTTGACCAGACTATACAGCA
    .         .         .         .         .         .
    LeuGlnGlyLeuThrIleGlnGluLeuProAspProProThrHisLeuProGluSerGln
    CysArgAspLeuLeuSerArgSerPheLeuThrLeuGluLeuIleTyrGlnAsnLeuArg
TCTGCAGGGACTTACTATCCAGGAGCTTCCTGACCCTCCAACTCATCTACCAGAATCTCA
    .         .         .         8500
ArgLeuAlaGluThr                       MetGlyAlaSerGlySerLysLys
    AspTrpLeuArgLeuArgThrAlaPheLeuGlnTyrGlyCysGluTrpIleGlnGluAla
GAGACTGGCTGAGACTTAGAACAGCCTTCTTGCAATATGGGTGCGAGTGGATCCAAGAAG
    .         .         .         .         .         .
    HisSerArgProProArgGlyLeuGlnGluArgLeuLeuArgAlaArgAlaGlyAlaCys
    PheGlnAlaAlaAlaArgAlaThrArgGluThrLeuAlaGlyAlaCysArgGlyLeuTrp
CATTCCAGGCCGCCGCGAGGGCTACAAGAGAGACTCTTGAGGGCGCGTGCAGGGGCTTCT
    .         8600        .         .         .         .
GlyGlyTyrTrpAsnGluSerGlyGluGluTyrSerArgPheGlnGluGlySerAspArg
    ArgValLeuGluArgIleGlyArgGlyIleLeuAlaValProArgArgIleArgGlnGly
GCAGCGTATTGGAACGAATCGGGAGGGGAATACTCGCGGTTCCAAGAAGGATCAGACAGC
    .         .         .         .         .         8700
GluGlnLysSerProSerCysGluGlyArgGlnTyrGlnGlnGlyAspPheMetAsnThr
    AlaGluIleAlaLeuLeu
GAGCAGAAAATCGCCCTCCTGTGAGGGACGGCAGTATCAGCAGGGAGACTTTATGAATACT
```

-continued

```
ProTrpLysAspProAlaAlaGluArgGluLysAsnLeuTyrArgGlnGlnAsnMetAsp
CCATGGAAGGACCCAGCAGCAGAAAGGGAGAAAAATTTGTACAGGCAACAAAATATGGAT
                              8800
AspValAspSerAspAspAspAspGlnValArgValSerValThrProLysValProLeu
GATGTAGATTCAGATGATGATGACCAAGTAAGAGTTTCTGTCACACCAAAAGTACCACTA

ArgProMetThrHisArgLeuAlaIleAspMetSerHisLeuIleLysThrArgGlyGly
AGACCAATGACACATAGATTGGCAATAGATATGTCACATTTAATAAAAACAAGGGGGGA
             8900
LeuGluGlyMetPheTyrSerGlyArgArgHisLysIleLeuAsnIleTyrLeuGluLys
CTGGAAGGGATGTTTTACAGTGAAAGAAGACATAAAATCTTAAATATATACTTAGAAAAG
                                                     9000
GluGluGlyIleIleAlaAspTrpGlnAsnTyrThrHisGlyProGlyValArgTyrPro
CAAGAAGGGATAATTGCAGATTGGCAGAACTACACTCATGGGCCAGGAGTAAGATACCCA

MetPhePheGlyTrpLeuTrpLysLeuValProValAspValProGlnGluGlyGluAsp
ATGTTCTTTGGGTGGCTATGGAAGCTAGTACCAGTAGATGTCCCACAAGAAGGGGAGGAC
                              9100
ThrGluThrHisCysLeuValHisProAlaGlnThrSerLysPheAspAspProHisGly
ACTGAGACTCACTGCTTAGTACATCCAGCACAAACAAGCAAGTTTGATGACCCGCATGGG

GluThrLeuValTrpGluPheAspProLeuLeuAlaTyrSerTyrGluAlaPheIleArg
GAGACACTAGTCTGGGAGTTTGATCCCTTGCTGGCTTATAGTTACGAGGCTTTTATTCGG
             9200
TyrProGluGluPheGlyHisLysSerGlyLeuProGluGluGluTrpLysAlaArgLeu
TACCCAGAGGAATTTGGGCACAAGTCAGGCCTGCCAGAGGAAGAGTGGAAGGCGAGACTG
                                               9300
LysAlaArgGlyIleProPheSer
AAAGCAAGAGCAATACCATTTAGTTAAAGACAGGAACAGCTATACTTGGTCAGGGCAGGA
       .         .         .         .         .         .
AGTAACTAACAGAAACAGCTGAGACTGCAGGGACTTTCCAGAAGGGGCTGTAACCAAGGG
                              9400
AGGGACATGGGAGGAGCTGGTGGGGAACGCCCTCATATTCTCTGTATAAATATACCCGCT
       .         .         .         .         .         .
AGCTTGCATTGTACTTCGGTCGCTCTGCGGAGAGGCTGGCAGATTGAGCCCTGGGAGGTT
             9500
CTCTCCAGCAGTAGCAGGTAGAGCCTGGGTGTTCCCTGCTAGACTCTCACCAGCACTTGG
                                                     9600
CCGGTGCTGGGCAGACGGCCCCACGCTTGCTTGCTTAAAAACCTCCTTAATAAAGCTGCC

AGTTAGAAGCA.
       .
```

\* \* \* \* \*

UNITED STATES PATENT AND TRADEMARK OFFICE
CERTIFICATE OF CORRECTION

PATENT NO. : 6,054,565
DATED : April 25, 2000
INVENTOR(S) : Marc Alizon, Luc Montagnier, Denise Geutard, Francois Clavel, Pierre Sonigo and Mireille Guyader It is certified that error appears in the above-identified patent and that said Letters Patent is hereby corrected as shown below:

Column 29,
Line 65, (320); "GACAGGGAC" should read -- GAACAGGGAC --

Column 30,
Line 65, (710); "CTCAAAAGAG" should read -- GTCAAAAGAG --

Column 31,
Line 20, (1010); "AACCCATAAT" should read -- AACCCTAAAT --

Column 32,
Line 4, (1820); "GACAAAGTGC" should read -- GACAAACTGC --

Column 33,
Line 29, (3320); "AHCCAHHAAC" should read -- AGCCAGGAAC --
Line 39, (3460); "AAAGACCCAT" should read -- AAACACCCAT --
Line 46, (3570); "GAGAAATCTC" should read -- GAGAAATCTG --

Column 34,
Line 62, (4910); "CACCYHHAHH" should read -- CACCTGGAGG --

Column 35,
Line 4, (5030); "GTGGACTTGT" should read -- GTGGACTTGC --
Line 26, (5380); "CCAGGAAAGA" should read -- CCAGGAAACA --
Line 31, (5450); "ACAGAGAACG" should read -- ACAGAGAAGC --
Line 35, (5600); "TTACCAAAGG" should read -- TTAGGAAAGG --
Line 40, (5620); "GTGGGGAGGG" should read -- CTGGGGAGGG --
Line 40, (5640); "AGGAGGGTCG" should read -- AGGAGGGTGG --
Line 45, (5720); "GGTGAATGGG" should read -- GGTGGATGGG --
Line 64, (6030); "CTCGTACCAT" should read -- CTGCTACCAT --

Column 36,
Line 24, (6430); "AGACAYCAAY" should read -- AGACATCAAT --
Line 39, (6680); "AAAAGAGTAT" should read -- AAAACAGTAT --
Line 56, (6940); "AAACHCAAAC" should read -- AAACGCAAAC --
Line 61, (7030); "TCATCAGCCT" should read -- TCATCAGCTT --

UNITED STATES PATENT AND TRADEMARK OFFICE
CERTIFICATE OF CORRECTION

PATENT NO.   : 6,054,565
DATED        : April 25, 2000
INVENTOR(S)  : Marc Alizon, Luc Montagnier, Denise Geutard, Francois Clavel, Pierre Sonigo and Mireille Guyader It is certified that error appears in the above-identified patent and that said Letters Patent is hereby corrected as shown below:

Column 37,
Line 61, (8130); "ATATTTTTGG" should read -- AATAGCTGGG --

Column 45,
Line 53, (between 5700 & 5800);
"LeuArgGluIleLysGluGluAlaLeuLysHisPheAspProArGleu...." should read
-- LeuArgGluIleLysGluGluAlaLeuLysHisPheAspProArgLeu .... --

Column 51,
Line 7, (between 8900 & 9000); "LeuGluGlyMetPheTyrSerGly...." should read
-- LeuGluGlyMetPheTyrSerGlu.... --

Signed and Sealed this

Thirtieth Day of July, 2002

Attest:

JAMES E. ROGAN
Attesting Officer          Director of the United States Patent and Trademark Office

UNITED STATES PATENT AND TRADEMARK OFFICE
CERTIFICATE OF CORRECTION

PATENT NO.   : 6,054,565
DATED        : April 25, 2000
INVENTOR(S)  : Marc Alizon et al.

It is certified that error appears in the above-identified patent and that said Letters Patent is hereby corrected as shown below:

Column 30,
Line 53, "AAGGGCTTGT" should read -- AAGGGCTTGC --.

Signed and Sealed this

Fifth Day of November, 2002

Attest:

Attesting Officer

JAMES E. ROGAN
Director of the United States Patent and Trademark Office